US012220554B2

(12) United States Patent
Uruma et al.

(10) Patent No.: US 12,220,554 B2
(45) Date of Patent: Feb. 11, 2025

(54) CONNECTION MEMBER, INJECTION DEVICE AND PUMP CASING EQUIPPED WITH CONNECTION MEMBER, AND LIQUID VERIFICATION METHOD USING CONNECTION MEMBER

(71) Applicant: DAIKEN MEDICAL CO., LTD., Osaka (JP)

(72) Inventors: Masayuki Uruma, Osaka (JP); Kazuki Ishibashi, Osaka (JP)

(73) Assignee: DAIKEN MEDICAL CO., LTD., Osaka (JP)

( * ) Notice: Subject to any disclaimer, the term of this patent is extended or adjusted under 35 U.S.C. 154(b) by 800 days.

(21) Appl. No.: 17/273,084

(22) PCT Filed: Aug. 28, 2019

(86) PCT No.: PCT/JP2019/033791
§ 371 (c)(1),
(2) Date: Mar. 3, 2021

(87) PCT Pub. No.: WO2020/054433
PCT Pub. Date: Mar. 19, 2020

(65) Prior Publication Data
US 2021/0268256 A1 Sep. 2, 2021

(30) Foreign Application Priority Data
Sep. 11, 2018 (JP) .................................. 2018-169671

(51) Int. Cl.
*A61M 39/12* (2006.01)
*A61M 5/142* (2006.01)
*A61M 39/10* (2006.01)

(52) U.S. Cl.
CPC ........ *A61M 39/12* (2013.01); *A61M 5/14224* (2013.01); *A61M 39/1011* (2013.01); *A61M 2039/1005* (2013.01); *A61M 2205/14* (2013.01)

(58) Field of Classification Search
CPC .... A61M 2039/1005; A61M 2205/121; A61M 2205/126; A61M 39/1011; A61M 1/152;
(Continued)

(56) References Cited

U.S. PATENT DOCUMENTS 4,657,490 A * 4/1987 Abbott ............. A61M 5/14224
417/478
4,722,224 A 2/1988 Scheller et al.
(Continued)

FOREIGN PATENT DOCUMENTS

CN 1573102 2/2005
JP 2002-517290 6/2002
(Continued)

OTHER PUBLICATIONS

Office Action issued May 24, 2022 in Chinese Patent Application No. 201980057851.0, with English-language translation.
(Continued)

*Primary Examiner* — Nathan R Price
*Assistant Examiner* — Kayla M. Turkowski
(74) *Attorney, Agent, or Firm* — Wenderoth, Lind & Ponack, L.L.P.

(57) ABSTRACT

Provided is a connection member which is not limited by the material, the tube thickness, the tube diameter or the like of a suction tube and a discharge tube to be connected to a pump, and can eliminate troubles in the tube attachment. A connection member includes: a pump attachment part; a tube connecting part; and a flow passage defining part. At least a portion of each of the suction passage section and the
(Continued)

discharge passage section of the flow passage defining part includes membranes deformable due to pressures of the liquid flowing in the suction passage section and the discharge passage section. The flow passage defining part has a shape allowing the flow passage defining part to be attached in an arrangement that the membranes face sensors for detecting a flow state of the liquid flowing in the suction passage section and the discharge passage section by deformation of the membranes.

12 Claims, 25 Drawing Sheets

(58) Field of Classification Search
CPC .......... A61M 1/36222; A61M 5/14224; A61M 5/14212; A61M 5/14586; A61M 39/12; A61M 2205/14; A61M 5/14; A61M 5/142
See application file for complete search history.

(56) References Cited

U.S. PATENT DOCUMENTS

| | | | |
|---|---|---|---|
| 4,758,228 | A | 7/1988 | Williams |
| 5,807,075 | A * | 9/1998 | Jacobsen ............... A61M 5/142 417/313 |
| 6,142,008 | A | 11/2000 | Cole et al. |
| 2002/0151838 | A1 | 10/2002 | Beck et al. |
| 2005/0019180 | A1 | 1/2005 | Seto et al. |
| 2008/0077068 | A1 | 3/2008 | Orr |
| 2008/0095651 | A1 | 4/2008 | Onishi |
| 2009/0118667 | A1 | 5/2009 | Haueter et al. |
| 2011/0125087 | A1 | 5/2011 | Sugimoto et al. |
| 2011/0309552 | A1 * | 12/2011 | Amirouche ....... A61M 5/16804 264/331.11 |
| 2012/0065596 | A1 | 3/2012 | Haueter et al. |
| 2012/0083735 | A1 * | 4/2012 | Pfouts ............... A61M 5/14232 604/151 |
| 2012/0224984 | A1 | 9/2012 | Orr |
| 2013/0144214 | A1 | 6/2013 | Amirouche et al. |
| 2014/0309589 | A1 | 10/2014 | Momose et al. |
| 2015/0098846 | A1 | 4/2015 | Orr |
| 2017/0312428 | A1 * | 11/2017 | Mizutani ............... A61M 5/365 |
| 2019/0085843 | A1 * | 3/2019 | Gabriel ............. A61M 5/14212 |
| 2019/0209768 | A1 | 7/2019 | Orr |
| 2019/0209769 | A1 | 7/2019 | Orr |
| 2019/0209770 | A1 | 7/2019 | Orr |
| 2019/0249656 | A1 | 8/2019 | Takahashi et al. |

FOREIGN PATENT DOCUMENTS

| | | |
|---|---|---|
| JP | 2009-525770 | 7/2009 |
| JP | 2010-209921 | 9/2010 |
| JP | 2010-242764 | 10/2010 |
| JP | 2011-131042 | 7/2011 |
| JP | 2014-200617 | 10/2014 |
| JP | 2015-128480 | 7/2015 |
| JP | 2016-101230 | 6/2016 |
| WO | 2018/079375 | 5/2018 |

OTHER PUBLICATIONS

Extended European Search Report issued Aug. 30, 2021 in corresponding European Patent Application No. 19860784.8.
International Search Report issued Oct. 21, 2019 in International (PCT) Application No. PCT/JP2019/033791.
Office Action issued Nov. 25, 2022 in corresponding Chinese Patent Application No. 201980057851.0, with partial English translation.

* cited by examiner

CONNECTION MEMBER, INJECTION DEVICE AND PUMP CASING EQUIPPED WITH CONNECTION MEMBER, AND LIQUID VERIFICATION METHOD USING CONNECTION MEMBER

TECHNICAL FIELD

The present invention relates to a connection member for connecting a tube with a pump, a pump casing and an injection device including the connection member, and a method for verifying liquid by use of the connection member.

BACKGROUND ART

For injection devices for injecting medical liquid to a patient, conventionally, there has been an injection device which is provided with a disposable pump unit as disclosed in Patent Literature 1. The injection device includes a main body 102 and a disposable part 103 being a disposable pump unit as shown in FIG. 25.

The main body 102 is formed in a surface thereof with a disposable part accommodation recess section 122 (hereinafter, referred to as recess section 122) where a pump main body 103*a* of the disposable part 103 is arranged, and a pair of tube accommodation grooves 123 respectively extending in an upstream side and a downstream side of the recess section 122.

Each of the pair of tube accommodation grooves 123 (hereinafter, referred to as groove 123) is provided with a pressure sensor 124. The pressure sensor 124 includes a movable block 1241 movable in accordance with a pressure fluctuation in the tube. Further, the groove 123 in the upstream side of the recess section 122 is provided with an air bubble sensor 125.

The disposable part 103 includes: the pump main body 103*a* having a diaphragm pump driven by a piezoelectric element; a suction tube 133 connected to a suction port 103*b* of the pump main body 103*a*; and a discharge tube 134 connected to a discharge port 103*c* of the pump main body 103*a*.

The suction tube 133 is fitted in the groove 123 in the upstream side of the recess section 122, and further tightly fitted in a groove formed in the movable block 1241 of the pressure sensor 124 to ensure an accurate measurement of pressure. Besides, the suction tube 133 is arranged so as to face a detection section of the air bubble sensor 125. Similarly, the discharge tube 134 is fitted in the groove 123 in the downstream side of the recess section 122, and further tightly fitted in a groove formed in the movable block 1241 of the pressure sensor 124.

The suction tube 133 includes a connecting port 1331 which is connected to a container containing medical liquid. The discharge tube 134 includes a connecting port 1341 to which a patient side tube is connected.

In the injection device configured as described above, when medical liquid is injected to a patient, a disposable part 103 which is to be disposed is first attached to the main body 102 as described above, and then the medical liquid is injected.

In a case where the medical liquid does not smoothly flow in the upstream side of the pump main body 103*a* due to bending of the suction tube 133 or the like during the medical liquid injection, a pressure drop in the suction tube 133 is detected by the pressure sensor 124 in the upstream side, and concurrently, the air bubble sensor 125 detects whether or not air bubble mixing occurs. A control part of the injection device performs controls of the injection device such as stopping of the pumping operation and giving of an alarm after receiving these detection signals. On the other hand, in a case where the medical liquid does not smoothly flow in the downstream side of the pump main body 103*a* due to a situation where the flow of medical liquid is impeded in the patient, a pressure rise in the discharge tube 134 is detected by the pressure sensor 124 in the downstream side, and the control part performs a control for stopping the pumping operation and giving an alarm after receiving the detection signal.

In the injection device disclosed in Patent Literature 1, the suction tube 133 and the discharge tube 134 are fitted in the groove 123 in the main body 102, and are further required to be tightly fitted in the groove formed in the movable block 1241 of the pressure sensor 124 in order to accurately measure a pressure depending on expansion and contraction of these tubes. Besides, the suction tube 133 is required to be arranged so as to face the detection section of the air bubble sensor 125. Accordingly, these tubes 133, 134 are required to be made of a particular material or a soft material such as silicone rubber which can come into close contact with the pressure sensor 124 and the air bubble sensor 125. Additionally, these tubes 133, 134 should be produced under conditions that the thickness and the diameter of the tubes 133, 134 are within a predetermined tolerance. As a result, there has been the problem that the tubes 133, 134 involve the limitation in materials and dimensions.

Besides, when the disposable part 103, which is a pump unit, is attached to the main body 102, the attachment of the tubes 133, 134 should be properly accomplished in the state where the tubes 133, 134 are made in close contact with the pressure sensor 124 and the air bubble sensor 125. Thus, there has been the problem that the attachment of tubes is very troublesome.

CITATION LIST

Patent Literature

Patent Literature 1: Japanese Unexamined Patent Publication No. 2016-101230

SUMMARY OF INVENTION

The present invention has been worked out in order to solve the problems, and has an object of providing a connection member which is not limited by the material, the tube thickness, the tube diameter or the like of a suction tube and a discharge tube to be connected to a pump, and can eliminate the troubles in the tube attachment.

A connection member according to an aspect of the present invention is provided between a pump for pressurizing and feeding liquid and a suction tube for connecting a suction port of the pump with the suction tube, and between the pump and a discharge tube for connecting a discharge port of the pump with the discharge tube, comprising: a pump attachment part which includes a suction opening for connection with the suction port and a discharge opening for connection with the discharge port, and which is attached with the pump in a state where the suction port is connected to the suction opening and the discharge port is connected to the discharge opening; a tube connecting part including a suction connecting section for connecting the suction tube and a discharge connecting section for connecting the discharge tube; and a flow passage defining part including a suction passage section and a discharge passage section, the suction passage section connecting the suction opening of the pump attachment part and the suction connecting section of the tube connecting part with each other so as to flow the liquid between the suction opening and the suction connecting section, and the discharge passage section connecting the discharge opening of the pump attachment part and the discharge connecting section of the tube connecting part with each other so as to flow the liquid between the discharge opening and the discharge connecting section, wherein at least a portion of each of the suction passage section and the discharge passage section includes a membrane deformable due to pressure of the liquid flowing in the suction passage section and the discharge passage section, and the flow passage defining part has a shape allowing the flow passage defining part to be attached to a sensor for detecting a flow state of the liquid flowing in the suction passage section and the discharge passage section by deformation of the membranes in an arrangement that the membranes face the sensor.

A pump casing according to another aspect of the present invention comprises: the connection member in which the flow passage defining part includes a suction sealing portion formed integrally with the suction passage section for ensuring liquid-tight sealing between the suction port of the pump and the suction opening of the pump attachment part, and a discharge sealing portion formed integrally with the discharge passage section for ensuring liquid-tight sealing between the discharge port of the pump and the discharge opening of the pump attachment part; and a lid member for closing a recess section of the pump attachment part, the recess section being for that the pump is inserted, wherein the suction sealing portion and the discharge sealing portion have the same height, the recess section is provided with at least one pump fixing portion having the same height as each height of the suction sealing portion and the discharge sealing portion, and the lid member has protrusions respectively protruding toward the suction sealing portion, the discharge sealing portion, and the pump fixing portion.

An injection device according to another aspect of the present invention is adapted for injecting liquid into an injection target, and comprises: a pump for pressurizing and feeding the liquid; a suction tube; a discharge tube; the connection member; and an injection device main body which holds the sensor and includes a mounted part on which the connection member is mounted, wherein the connection member includes a fitting section for fitting to a fitted section provided in the mounted part in a state where the membranes face the sensor.

A method for verifying liquid according to another aspect of the present invention is for verifying presence of liquid by use of the connection member, and comprises: a preparation step of disposing the connection member in a position to allow the sensor for detecting presence of air to face the membrane of the suction passage section in a state where the pump is attached to the pump attachment part and further the suction tube and the discharge tube are respectively attached to the suction connecting section and the discharge connecting section of the tube connecting part; and a detection step of detecting an absence of the liquid by detecting, with the sensor, air in a gap produced between the membranes and the sensor by denting of the membranes due to run-out of the liquid in the suction passage section during a time when the pump pressurizes and feeds the liquid from the suction tube to the discharge tube through the connection member.

DESCRIPTION OF EMBODIMENTS

Hereinafter, a preferred embodiment of the present invention will be described with reference to the drawings.

Figure 1:
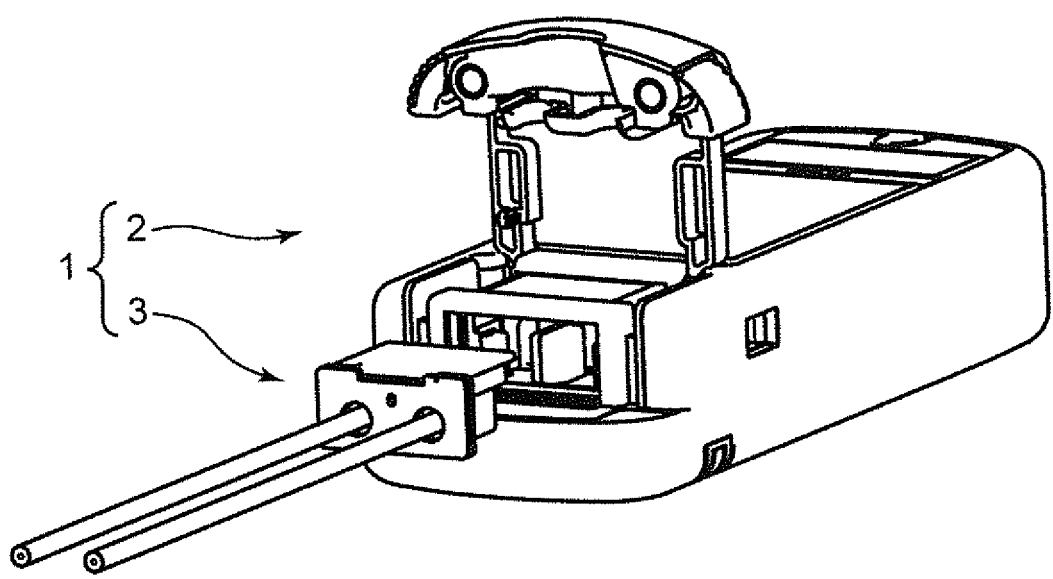
FIG. 1 is a perspective view of an injection device according to an embodiment of the present invention.

As shown in FIG. 1, an injection device 1 according to an embodiment of the present invention is adapted for injecting liquid into an injection target, and in the present embodiment is configured to be portable as an injection device for injecting medical liquid in a patient. The injection device 1 includes an injection device main body 2, and a disposable pump unit 3.

Figure 2:
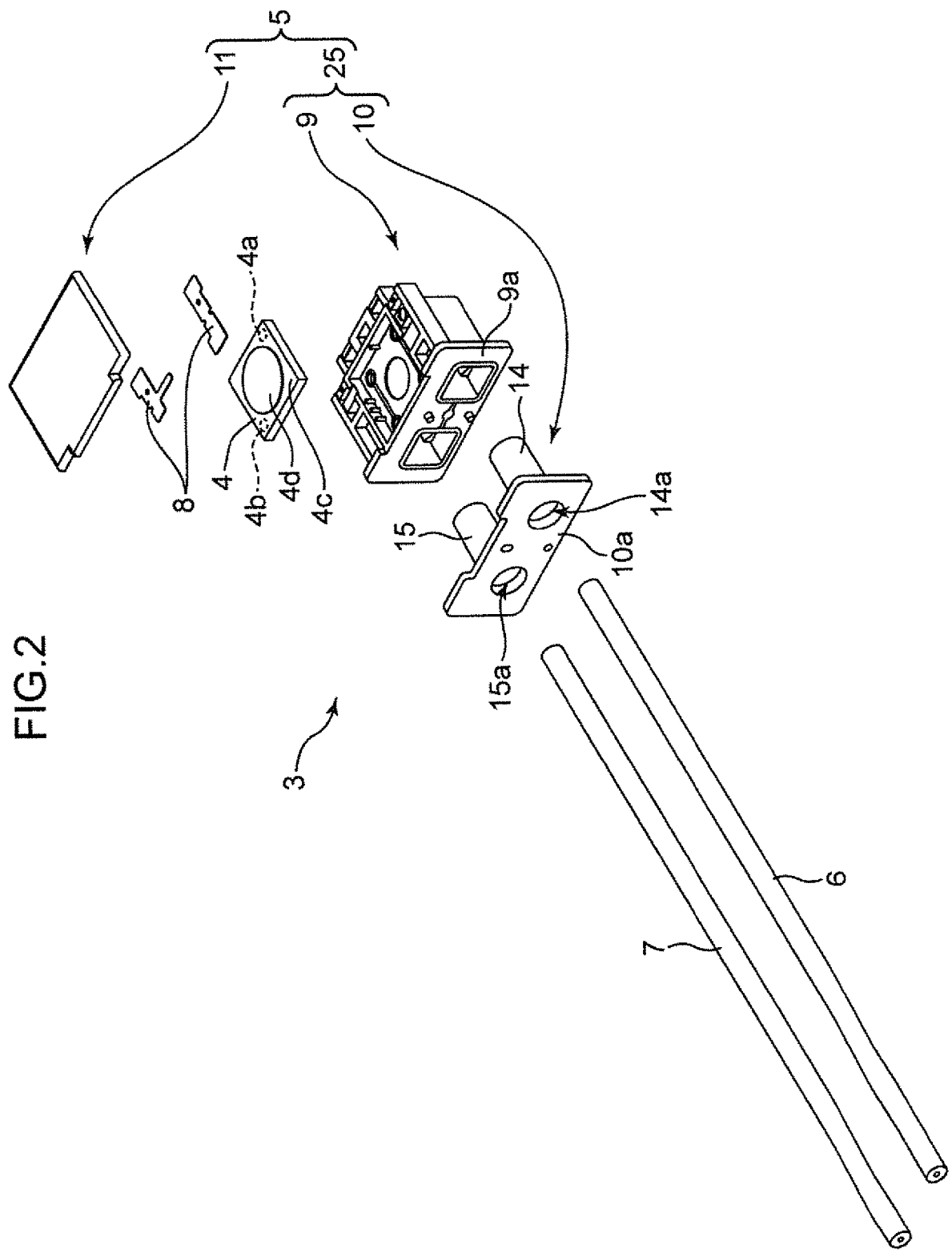
FIG. 2 is an exploded perspective view of a pump unit shown in FIG. 1.

The pump unit 3 includes a pump casing 5 having a connection member 25 according to the embodiment of the present invention as shown in FIG. 2. Specifically, the pump unit 3 includes a diaphragm pump 4 serving as a pump for pressurizing and feeding medical liquid, a pump casing 5 accommodating the diaphragm pump 4, a suction (aspiration) tube 6, a discharge tube 7, and an electrode 8 for electrically connecting the diaphragm pump 4 to an electric circuit provided in the injection device main body 2.

The pump for pressurizing and feeding the medical liquid may be a pump different from the diaphragm pump 4 described above, and in that case a disposable inexpensive pump is preferable.

The diaphragm pump 4 is of a pulsatile type which contains a diaphragm and a piezoelectric element for reciprocatingly vibrating the diaphragm in a flat casing, and includes a suction port 4a and a discharge port 4b which open in a bottom wall of the flat casing. The diaphragm pump 4 has a stationary section 4c (specifically, a flame section) which is immovable when the liquid is pressurized and fed, and a movable section 4d (specifically, a diaphragm which expands and contracts up and down). The suction port 4a and the discharge port 4b are formed in the bottom wall of the stationary section 4c.

The pump casing 5 includes a casing main body 9, a tube connecting part 10, and a lid member 11 as shown in FIGS. 2 to 8. The casing main body 9 and the tube connecting part 10 constitute a connection member 25 according to the embodiment of the present invention. The connection member 25 is provided between the diaphragm pump 4, the suction tube 6, and the discharge tube 7 to connect a suction port 4a of the pump 4 with the suction tube 6, and a discharge port 4b of the pump 4 with the discharge tube 7.

The tube connecting part 10 is attached in a front surface 9a of the casing main body 9. The tube connecting part 10 has a structure to allow each of the suction tube 6 and the discharge tube 7 to be connected therewith. Specifically, the tube connecting part 10 includes a suction connecting section 14 to be connected to the suction tube 6 and a discharge connecting section 15 to be connected to the discharge tube 7. The suction connecting section 14 and the discharge connecting section 15 each have the shape of a cylinder, and are formed integrally with a front flange 10a of the tube connecting part 10. The suction connecting section 14 and the discharge connecting section 15 have tube connecting front ports 14a, 15a and rear ports 14b, 15b, respectively. The suction tube 6 and the discharge tube 7 are respectively inserted in the tube connecting front ports 14a, 15a, and then fixed by an adhesive and the like.

The casing main body 9 includes a pump attachment part 12 and a flow passage defining part 13 as shown in FIGS. 9 to 17.

The pump attachment part 12 includes a recess section 12a having an upper surface where the diaphragm pump 4 is to be attached. The diaphragm pump 4 is accommodated in the recess section 12a, and fixed in the recess section 12a by welding or bonding the lid member 11 to the casing main body 9. Fixation of the diaphragm pump 4 is described in detail in the below-described Feature of Present Embodiment (7). The recess section 12a is closed by the lid member 11 (see FIGS. 2 to 6), and the diaphragm pump 4 is thus protected from external foreign substances or moisture. A suction opening 12b and a discharge opening 12c are formed in a bottom wall of the recess section 12a at a position corresponding to the suction port 4a and the discharge port 4b of the diaphragm pump 4 (see FIG. 2). Also, the flow passage defining part 13 is formed with a suction connecting port 20, a suction sealing portion 22, a discharge connecting port 21, and a discharge sealing portion 23 as described later. These are respectively inside the suction opening 12b and the discharge opening 12c and face the suction port 4a and the discharge port 4b of the diaphragm pump 4. Owing to this configuration of the pump attachment part 12, the diaphragm pump 4 is attached on the recess section 12a of the pump attachment part 12 in a state where the suction port 4a of the diaphragm pump 4 is connected with the suction opening 12b, and the discharge port 4b of the diaphragm pump 4 is connected with the discharge opening 12c.

The pump attachment part 12 is preferably made of a hardly deformable material such as a hard synthetic resin. Accordingly, in the attachment of the pump unit 3 to the injection device main body 2, the flow passage defining part 13 (particularly, the membranes 16a and 17a of the suction passage section 16 and the discharge passage section 17) can be accurately positioned at the positions facing an air bubble sensor 37 and a closure sensor 38 (see FIGS. 18 to 24) of the injection device main body 2 which will be described later.

The pump attachment part 12 has a shape which is insertable in a space 33b (see FIGS. 18 and 19) above a below-described protruding section 34 formed on a pump mounted part 33 of the injection device main body 2. Besides, a below-described restricting section 12d is provided on a rear side portion of the pump attachment part 12.

The flow passage defining part 13 includes a suction passage section 16 and a discharge passage section 17. The suction passage section 16 is configured to communicate the suction port 4a of the diaphragm pump 4 and the suction connecting section 14 of the tube connecting part 10 with each other so as to flow the medical liquid between the suction port 4a and the suction connecting section 14. The discharge passage section 17 is configured to communicate the discharge port 4b of the diaphragm pump 4 and the discharge connecting section 15 of the tube connecting part 10 with each other so as to flow the medical liquid between the discharge port 4b and the discharge connecting section 15.

In this embodiment, specifically, the suction passage section 16 and the discharge passage section 17 have the shape of a rectangular cylinder, and respectively have openings 16d, 17d in a front side, but closed in a rear side.

At least a portion of each of the suction passage section 16 and the discharge passage section 17 includes membranes 16a, 17a which is deformable due to pressure of the medical liquid flowing in the suction passage section 16 and the discharge passage section 17. In the present embodiment, the suction passage section 16 and the discharge passage section 17 are formed integrally with each other using a deformable soft material such as a silicone rubber. Accordingly, the suction passage section 16 and the discharge passage section 17, which are made of a silicone rubber and have the shape of a rectangular cylinder, constitute the deformable membranes 16a, 17a in all the peripheral wall including the opposite side walls. The suction passage section 16 and the discharge passage section 17 may be made to have the deformable membranes 16a, 17a in only the opposite side walls.

Figure 7:
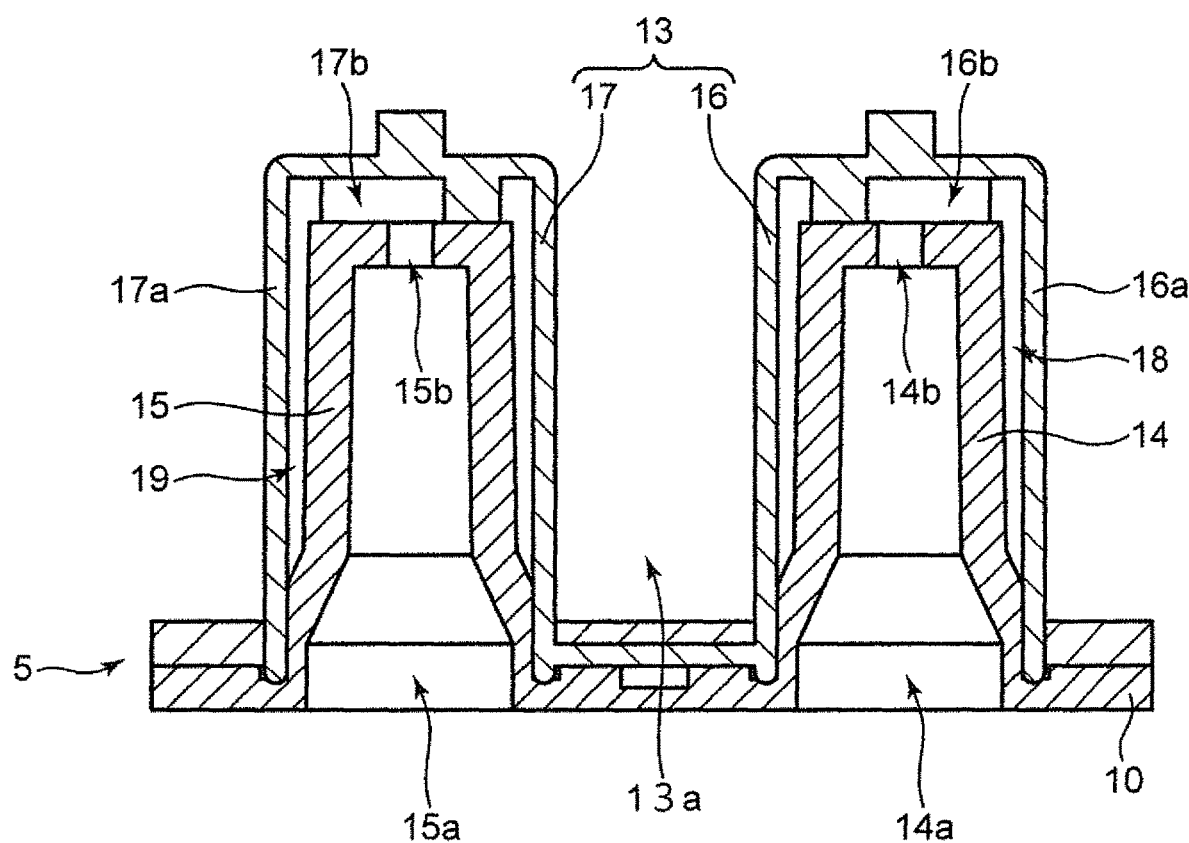
FIG. 7 is a cross sectional view taken along the line VII-VII in FIG. 4.
Figure 8:
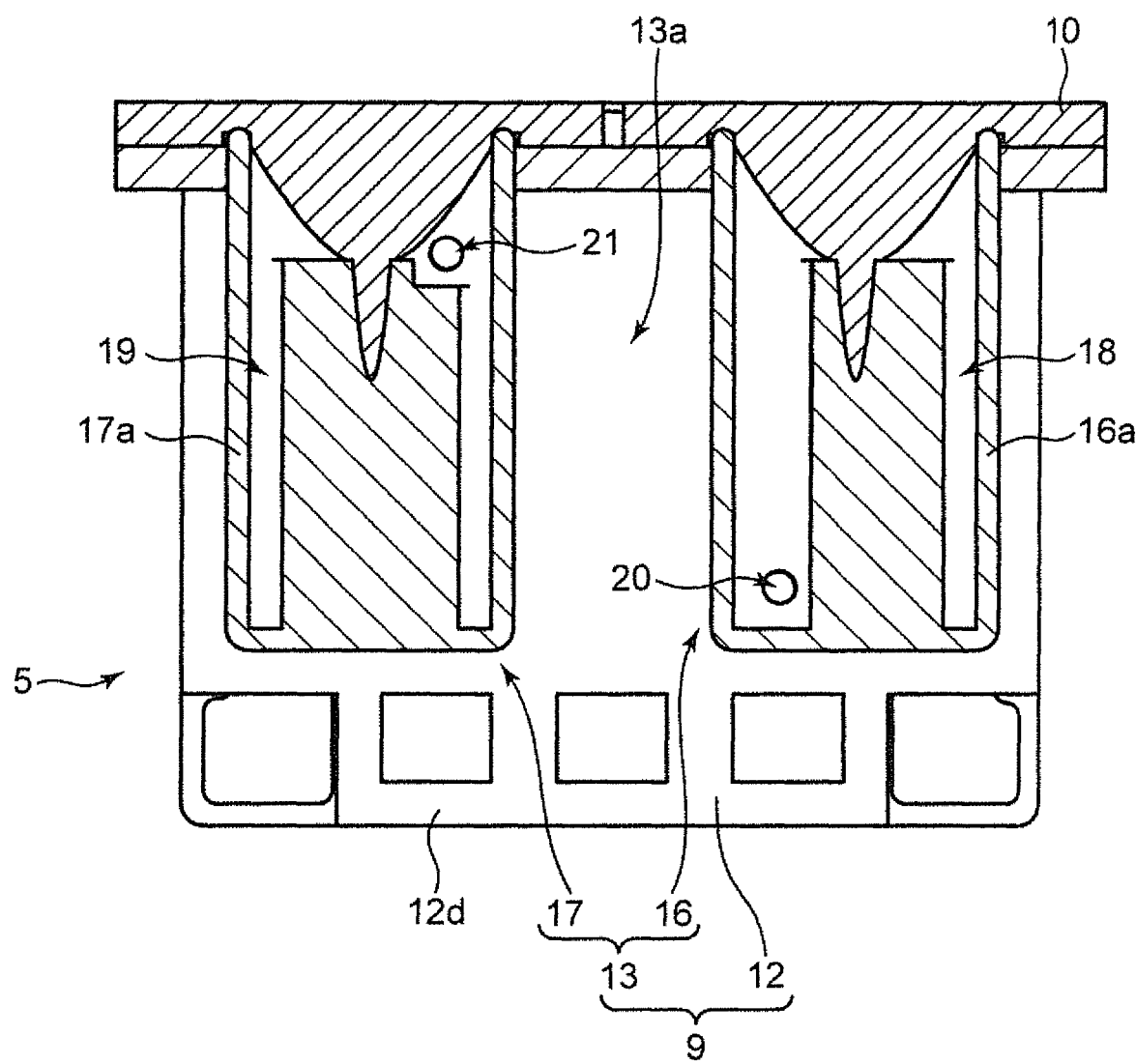
FIG. 8 is a cross sectional view taken along the line VIII-VIII in FIG. 4.

The flow passage defining part 13 has a shape allowing the flow passage defining part 13 to be attached in such an arrangement that the membranes 16a, 17a can face a sensor to detect by deformation of the membranes 16a, 17a a flow state of the medical liquid flowing in the suction passage section 16 and the discharge passage section 17, i.e., an air bubble sensor 37 and a closure sensor 38 in the present embodiment (see FIGS. 18 to 24). Specifically, the membranes 16a, 17a, respectively constituting the side wall of the suction passage section 16 and the discharge passage section 17, are exposed and spaced apart from each other. In a state where the suction passage section 16 and the discharge passage section 17 are respectively placed in a suction passage section insertion space 35 and a discharge passage section insertion space 36 of the pump mounted part 33 of the injection device main body 2 as shown in FIGS. 18 to 24, the membrane 16a of the suction passage section 16 lies between a pair of piezoelectric elements 37a, 37b of the air bubble sensor 37 (see FIG. 24). Besides, the side wall of the discharge passage section 17 is in contact with a closure sensor 38 (see FIG. 19). The side wall of the discharge passage section 17 is constituted by the membrane 17a as shown in FIGS. 7 to 8.

The flow passage defining part 13 includes a suction connecting port 20 for connecting the suction port 4a of the diaphragm pump 4 with the suction passage section 16, and a discharge connecting port 21 for connecting the discharge port 4b of the diaphragm pump 4 with the discharge passage section 17 as shown in FIGS. 8 to 9 and 14 to 17. Further, a suction sealing portion 22 for ensuring liquid-tight sealing between the suction port 4a of the diaphragm pump 4 and the suction opening 12b of the pump attachment part 12 is provided in a periphery of the suction connecting port 20. Besides, a discharge sealing portion 23 for ensuring liquid-tight sealing between the discharge port 4b of the diaphragm pump 4 and the discharge opening 12c of the pump attachment part 12 is provided in a periphery of the discharge connecting port 21. As described above, the suction connecting port 20 and the suction sealing portion 22 are connected to the suction port 4a of the diaphragm pump 4 through the suction opening 12b of the pump attachment part 12. Besides, the discharge connecting port 21 and the discharge sealing portion 23 are connected to the discharge port 4b of the diaphragm pump 4 through the discharge opening 12c of the pump attachment part 12.

Each of the combination of the membrane 16a of the suction passage section 16 and the suction sealing portion 22 and the combination of the membrane 17a of the discharge passage section 17 and the discharge sealing portion 23 is formed into one body by a flexible material, for example, a material such as a silicone rubber mentioned above.

Further, the combination of the membrane 16a of the suction passage section 16 and the suction sealing portion 22 and the combination of the membrane 17a of the discharge passage section 17 and the discharge sealing portion 23 each form a cylindrical member (in the present embodiment, a rectangular cylindrical body).

The cylindrical suction connecting section 14 (see FIGS. 2 to 7) of the tube connecting part 10 is inserted from a front opening 16d of the rectangular cylindrical suction passage section 16 into an inside of the suction passage section 16, and its upper and lower sides are supported by a support portion 16c (see FIGS. 5 to 6 and 10 to 14). Owing to this arrangement, the membrane 16a of the suction passage section 16 covers a periphery of the suction connecting section 14 with a gap to define a suction flow passage 18 (see FIGS. 7 to 8 and 24) between the suction connecting section 14 and the membrane 16a of the suction passage section 16.

The suction flow passage 18 communicates with the opening 14b of the suction connecting section 14 via a communication passage 16b of the suction passage section 16 (see FIG. 7). Besides, the suction flow passage 18 is connected to the suction port 4a of the diaphragm pump 4 via the suction connecting port 20 mentioned above.

Figure 10:
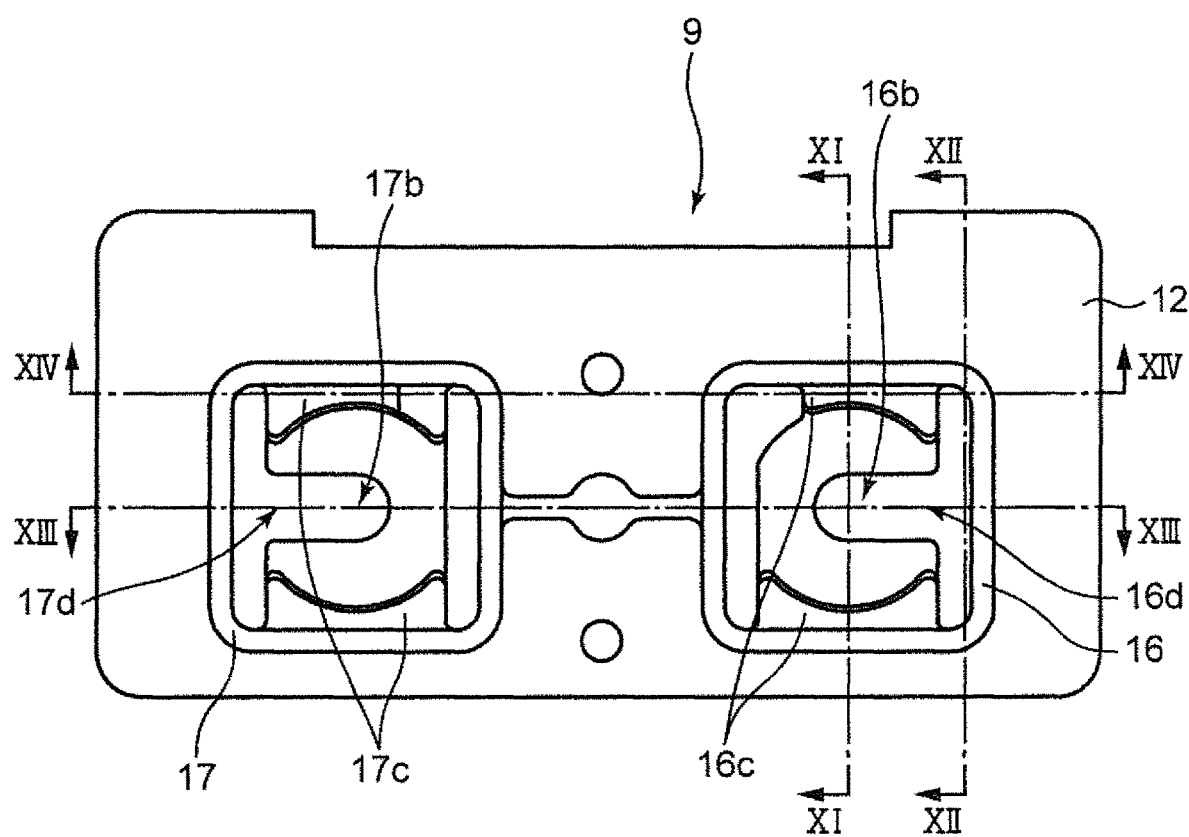
FIG. 10 is a front view of the casing main body shown in FIG. 9.
Figure 11:
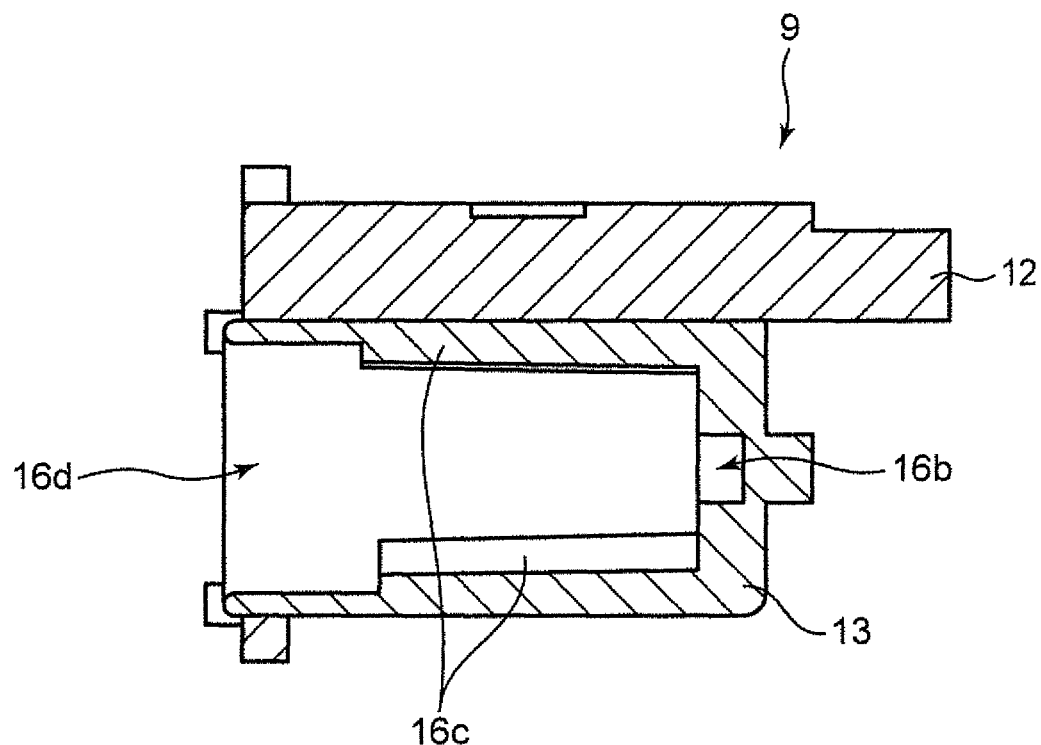
FIG. 11 is a cross sectional view taken along the line XI-XI in FIG. 10.
Figure 12:
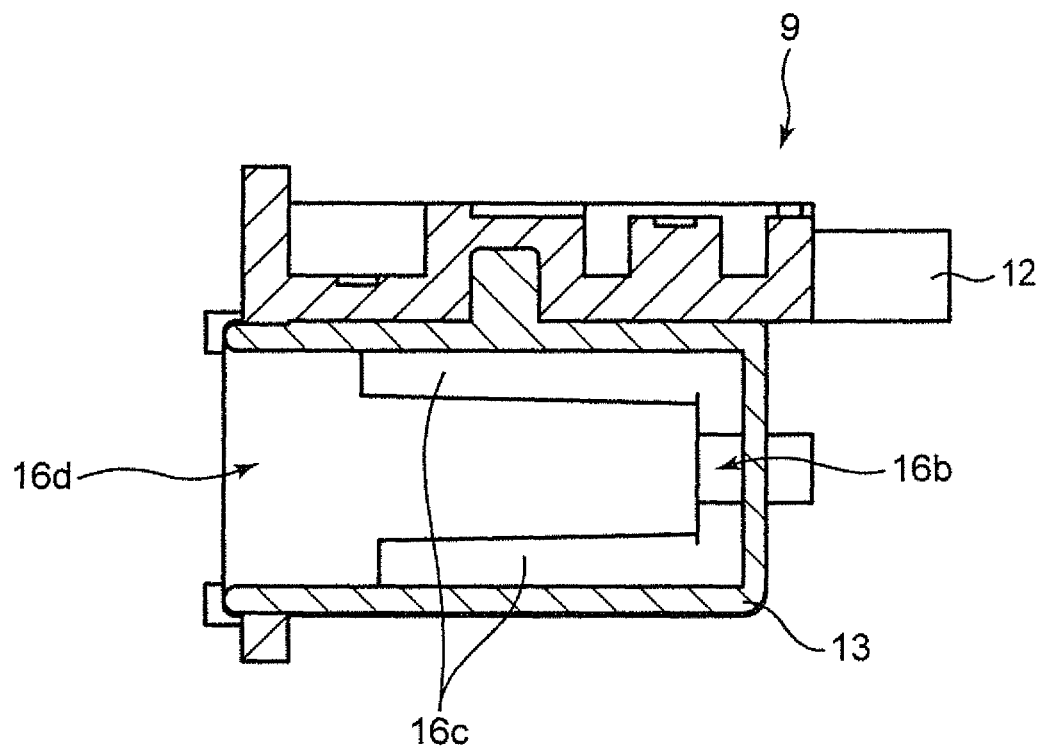
FIG. 12 is a cross sectional view taken along the line XII-XII in FIG. 10.
Figure 13:
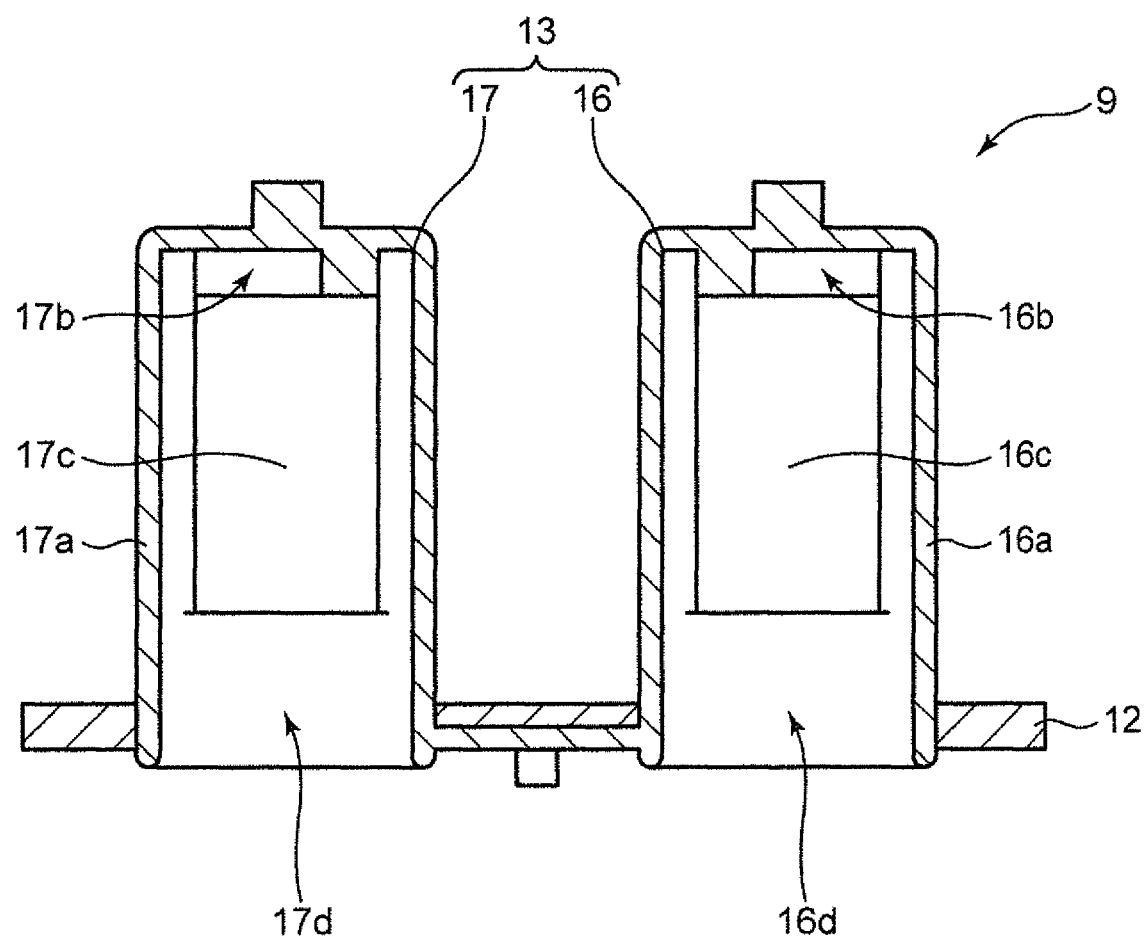
FIG. 13 is a cross sectional view taken along the line XIII-XIII in FIG. 10.
Figure 14:
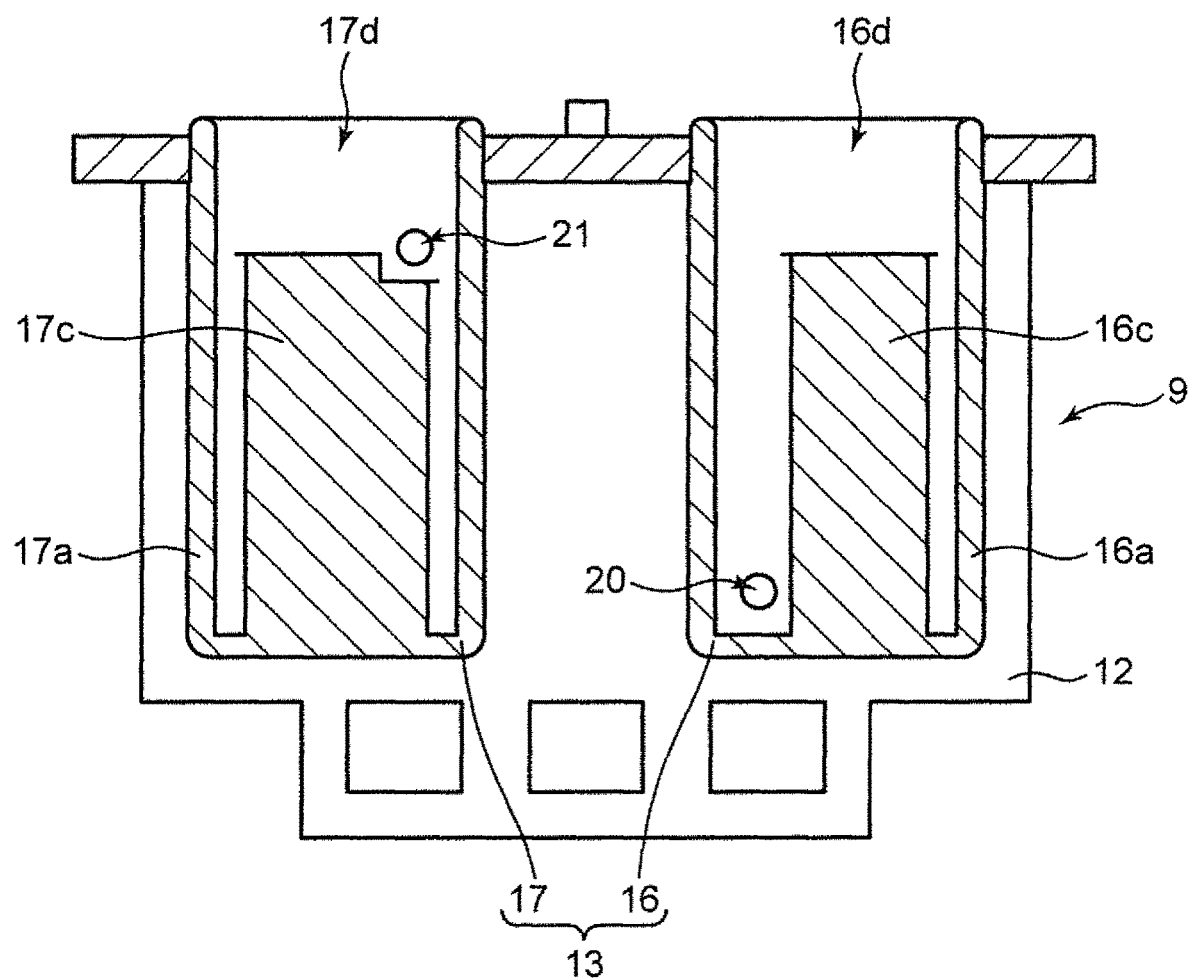
FIG. 14 is a cross sectional view taken along the line XIV-XIV in FIG. 10.

Similarly to the suction connecting section 14, the cylindrical discharge connecting section 15 is inserted from a front opening 17d of the rectangular discharge passage section 17 into an inside of the discharge passage section 17, and its upper and lower sides are supported by a support portion 17c (see FIGS. 10, and 13 to 14). Owing to this arrangement, the membrane 17a of the discharge passage section 17 covers a periphery of the discharge connecting section 15 with a gap to define a discharge flow passage 19 (see FIGS. 7 to 8) between the discharge connecting section 15 and the membrane 17a of the discharge passage section 17.

The discharge flow passage 19 communicates with the opening 15b of the discharge connecting section 15 via a communication passage 17b of the discharge passage section 17 (see FIG. 7). Besides, the discharge flow passage 19 is connected to the discharge port 4b of the diaphragm pump 4 via the discharge connecting port 21 mentioned above.

Accordingly, in the pump unit 3 of the present embodiment, the medical liquid suctioned from the suction tube 6 flows through the opening 14b of the suction connecting section 14, the communication passage 16b of the suction passage section 16, the suction flow passage 18, and the suction connecting port 20, in order, and then is introduced inside the pump 4 from the suction port 4a of the diaphragm pump 4.

Besides, the medical liquid discharged from the discharge port 4b of the diaphragm pump 4 flows through the discharge connecting port 21, the discharge flow passage 19, the communication passage 17b of the discharge passage section 17, and the opening 15b of the discharge connecting section 15, in order, and is discharged from the discharge tube 7.

As shown in FIGS. 7 to 8, the flow passage defining part 13 is provided with a gap 13a as a fitting section which fits to the protruding section 34 (see FIGS. 18 to 20, and 22) which is a fitted section formed in the injection device main body 2 where the pump casing 5 is placed between the suction passage section 16 and the discharge passage section 17. In other words, the connection member 25 (see FIG. 2) formed with the casing main body 9 including the flow passage defining part 13 is provided with a gap 13a (fitting section) which fits to the protruding section 34 (fitted section) of the injection device main body 2 holding the air bubble sensor 37 and the closure sensor 38 in a state where the membranes 16a, 17a face the sensors.

Further, the pump attachment part 12 includes a restricting section 12d for keeping the gap 13a (the fitting section) described above from fitting to the protruding section 34 (the fitted section) described above in a state where the membranes 16a, 17a of the flow passage defining part 13 do not face the air bubble sensor 37 and the closure sensor 38. The restricting section 12d has a shape which comes into the space over the aforementioned gap 13a in the rear side portion of the pump attachment part 12. When the pump casing 5 is mounted in the pump mounted part 33 of the injection device main body 2 in a posture of upside down, the restricting section 12d comes into contact with the protruding section 34, thereby keeping the gap 13a from fitting to the aforementioned protruding section 34 in a state where the membranes 16a, 17a of the flow passage defining part 13 do not face the air bubble sensor 37 and the closure sensor 38.

When the pump casing 5 is mounted in the pump mounted part 33 in the correct direction, the restricting section 12d of the pump attachment part 12 is inserted in the space 33b over the protruding section 34. The aforementioned gap 13a can thus fit to the protruding section 34 in the state where the membranes 16a, 17a face the air bubble sensor 37 and the closure sensor 38.

Figure 18:
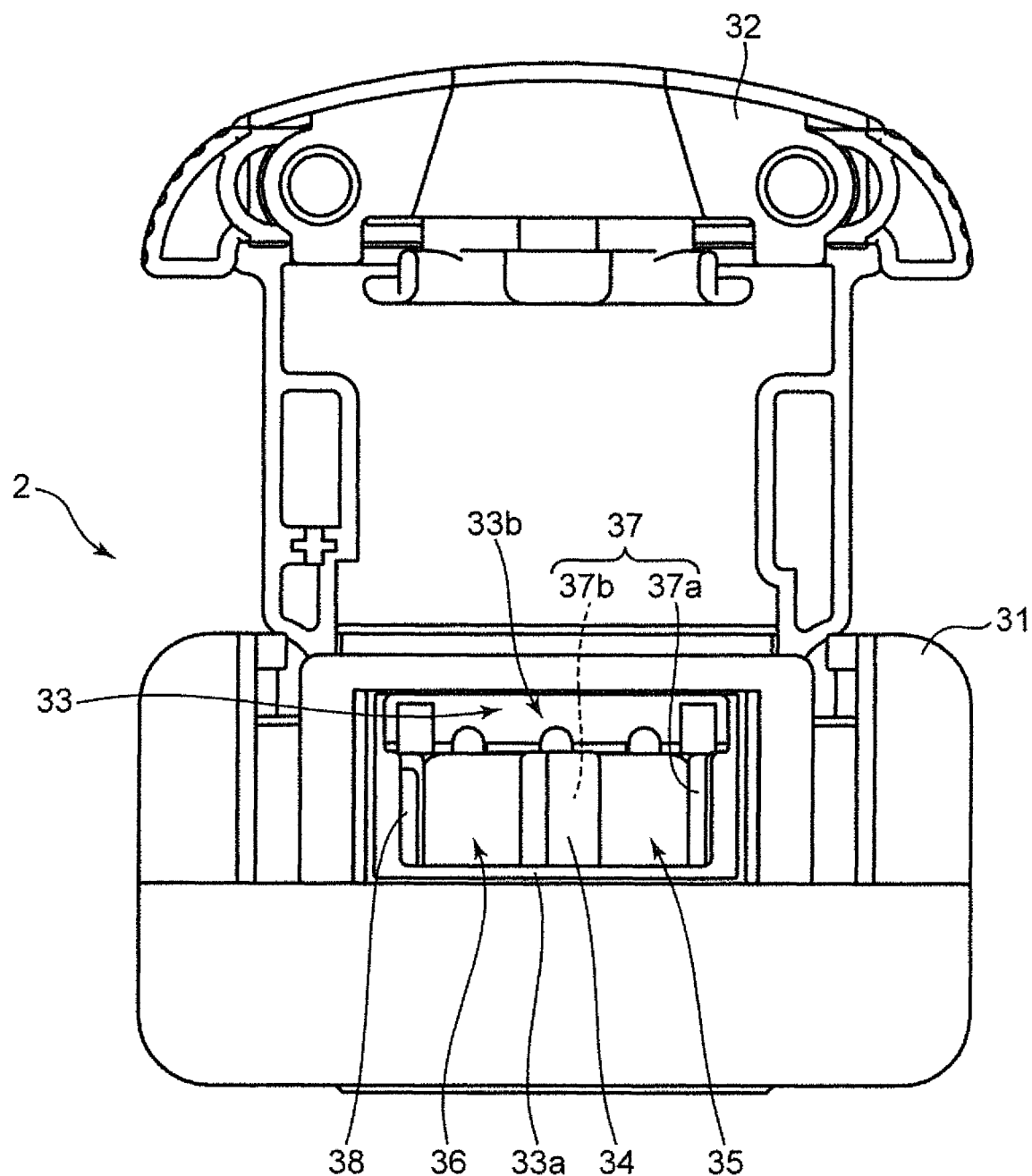
FIG. 18 is a front view showing a pump mounted part in a state where a cover of an injection device main body shown in FIG. 1 is open.
Figure 19:
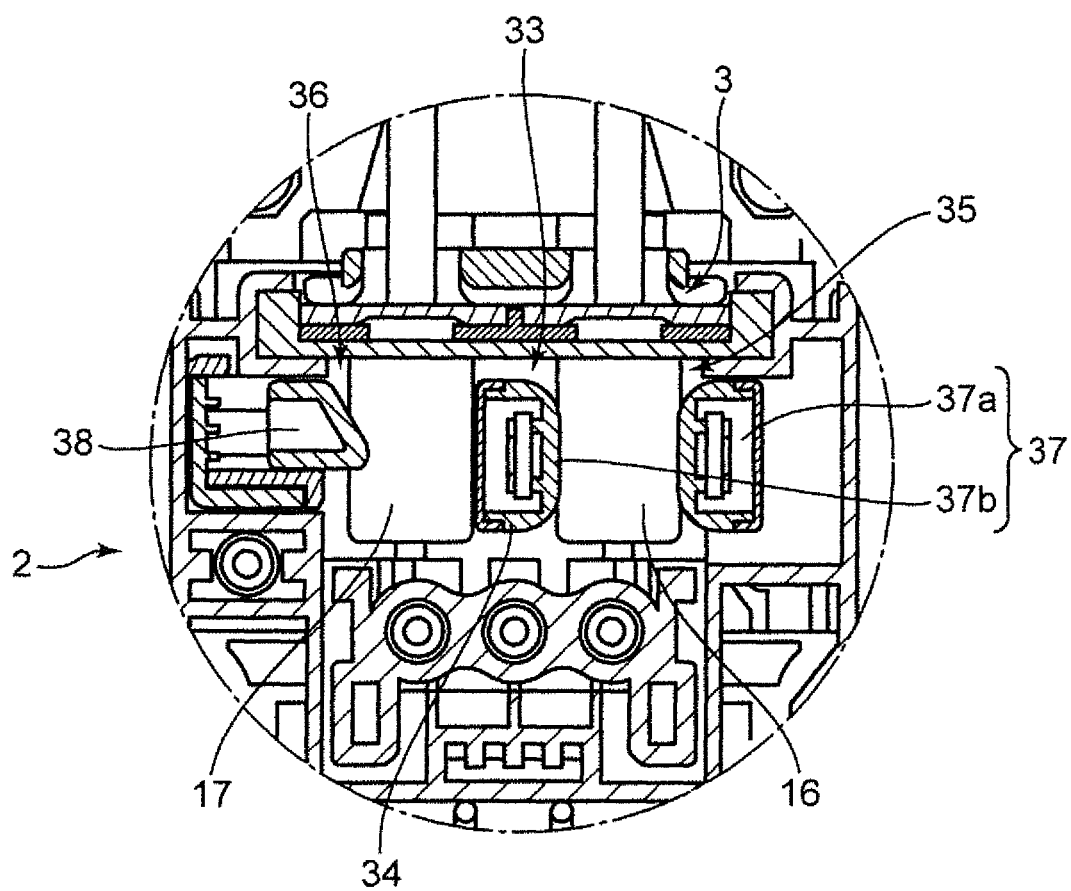
FIG. 19 is a cross sectional view illustrating a state where a pump unit is mounted on the pump mounted part shown in FIG. 18 in a horizontal cross section.
Figure 20:
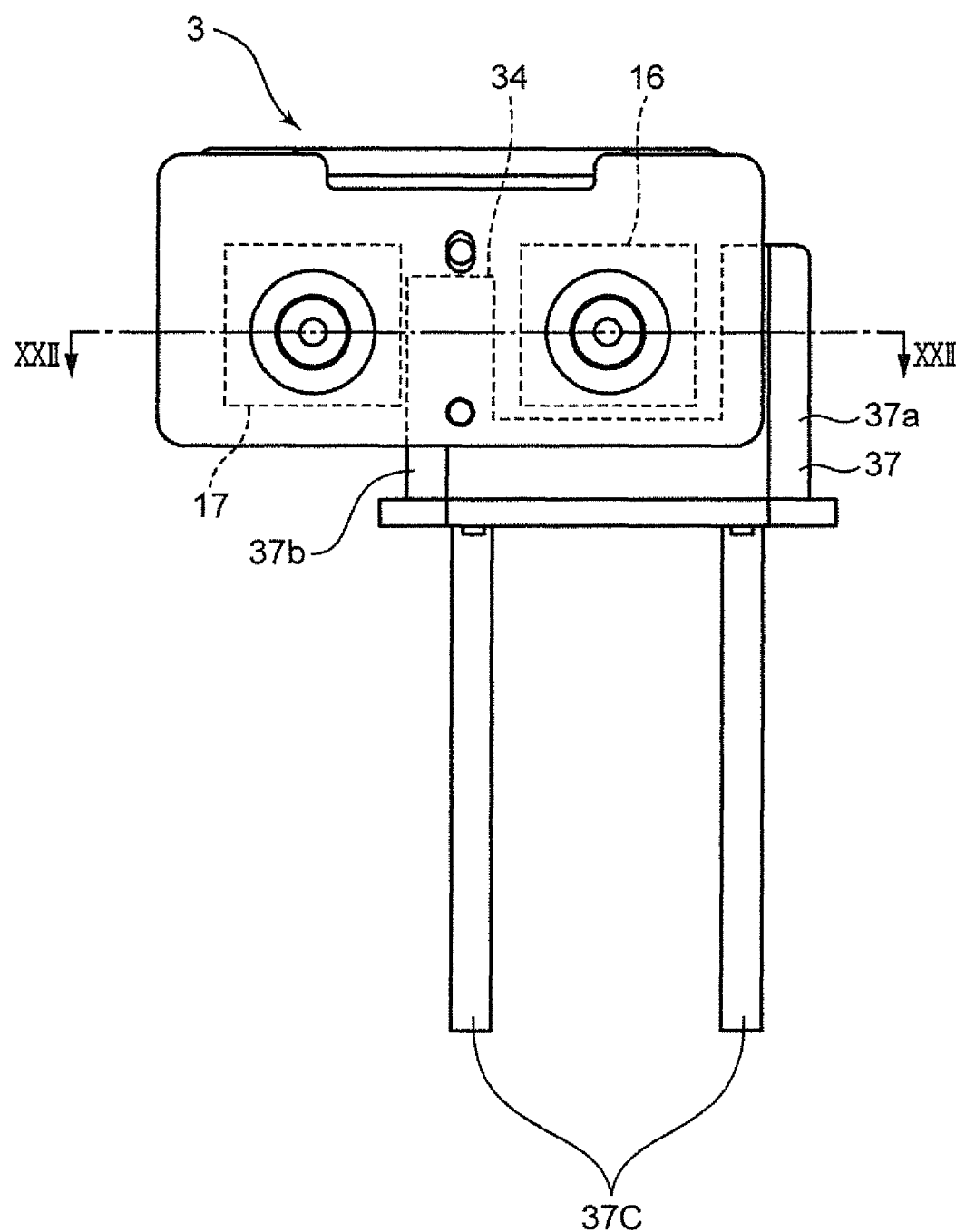
FIG. 20 is a front view of the pump unit shown in FIG. 19, showing a positional relationship between a suction passage section, a discharge passage section, and a pair of piezoelectric elements of an air bubble sensor.
Figure 21:
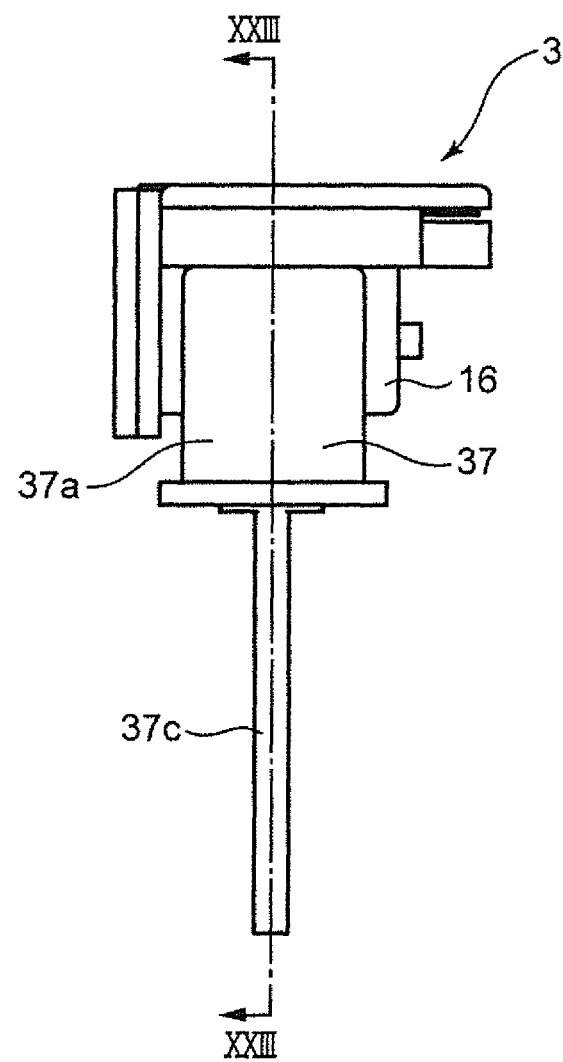
FIG. 21 is a side view of the pump unit shown in FIG. 19, showing a positional relationship between the suction passage section and the piezoelectric elements of the air bubble sensor.
Figure 22:
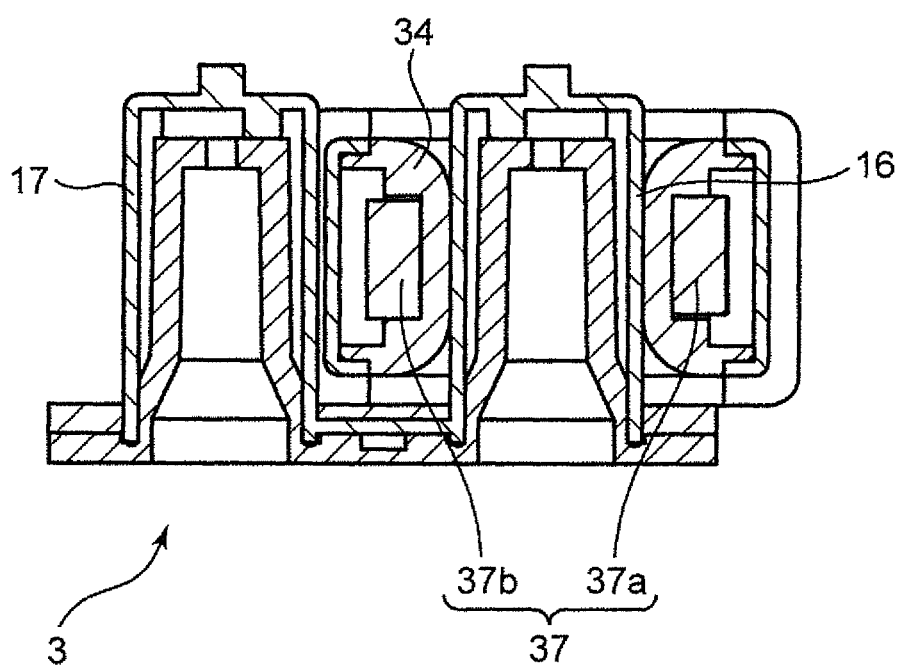
FIG. 22 is a cross sectional view taken along the line XXII-XXII in FIG. 20.
Figure 23:
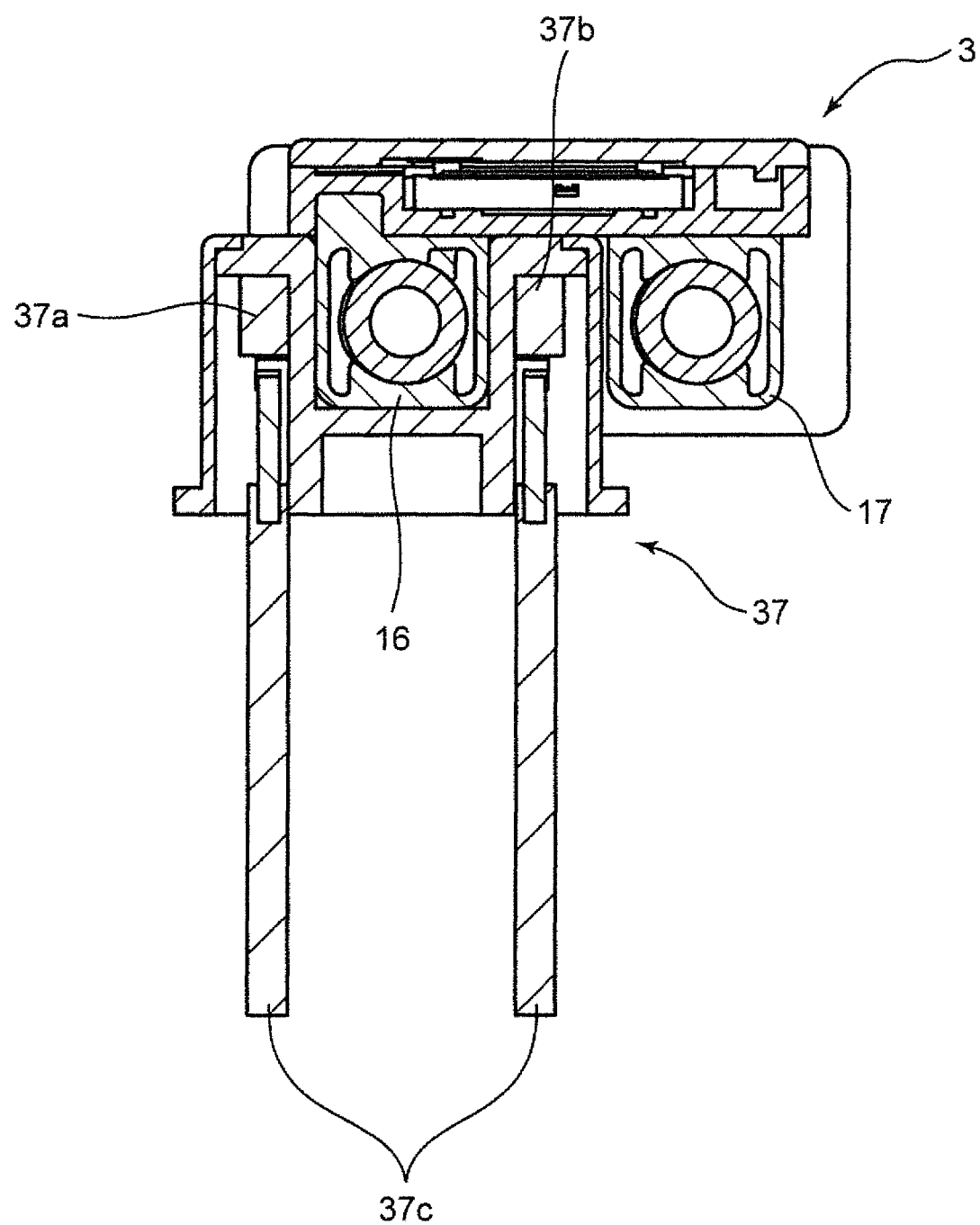
FIG. 23 is a cross sectional view taken along the line XXIII-XXIII in FIG. 21.
Figure 24:
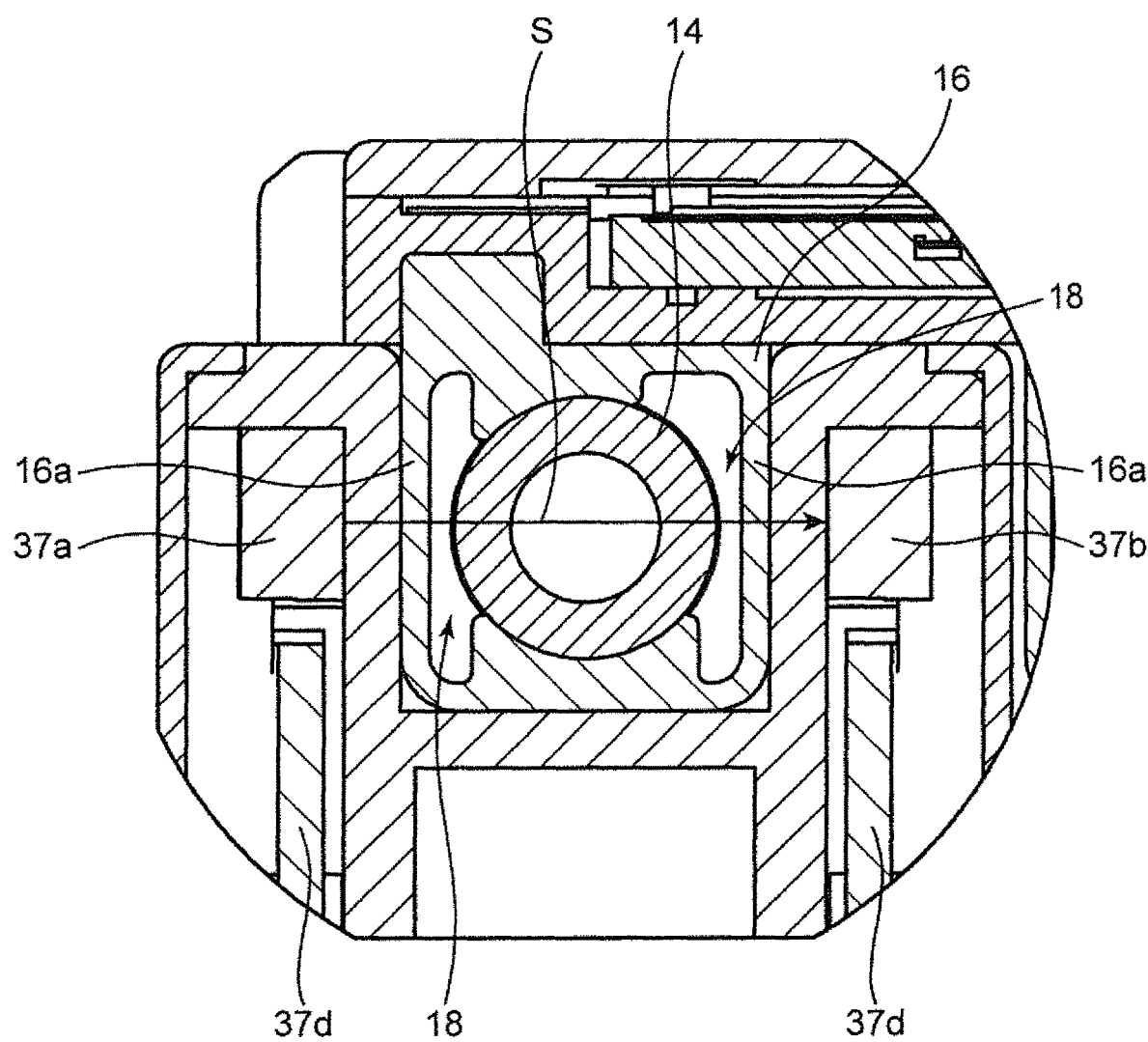
FIG. 24 is an enlarged cross sectional view of the pair of piezoelectric elements and a vicinity of membranes shown in FIG. 23.
Figure 25:
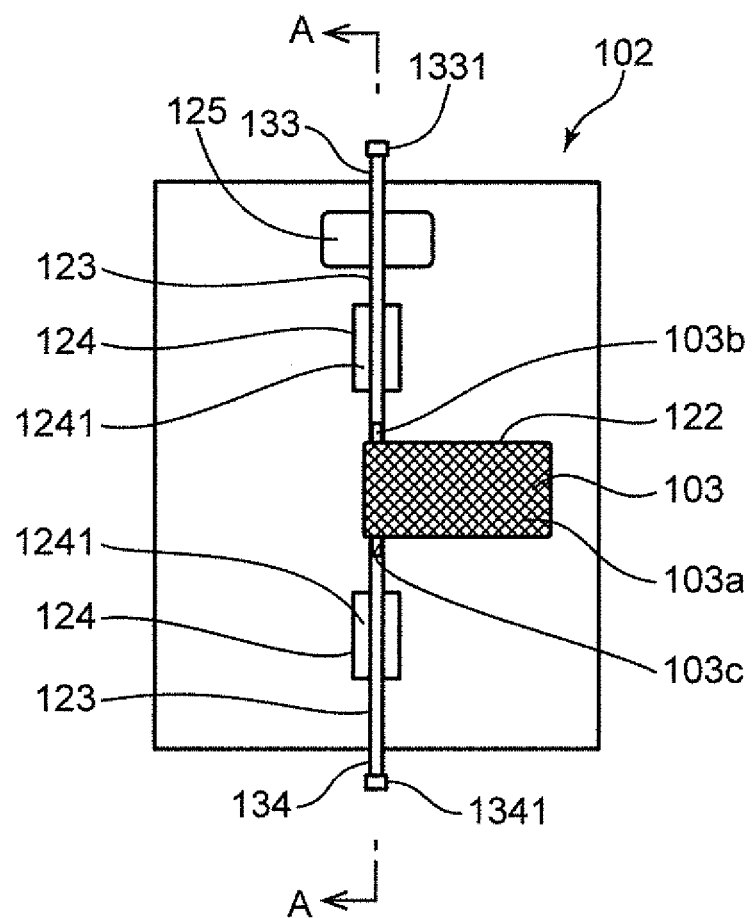
FIG. 25 is a plan view schematically showing a structure of a conventional injection device.

The injection device main body 2 includes a main body case 31, a cover 32, the pump mounted part 33, the protruding section 34, the air bubble sensor 37, and the closure sensor 38 as shown in FIGS. 18 to 19.

The pump mounted part 33 has a space which is provided in the main body case 31, and in which the pump casing 5 of the pump unit 3 is placed. An entrance of the pump mounted part 33 is openably closed by the cover 32. The protruding section 34 (fitted section) is arranged on a bottom wall 33a (see FIG. 18) of the pump mounted part 33, and protrudes upward from the bottom wall 33a. The suction passage section insertion space 35 and the discharge passage section insertion space 36 described above are formed in both sides of the protruding section 34 in the pump mounted part 33. The suction passage section 16 and the discharge passage section 17 are individually accommodated in the spaces 35, 36 while being spaced apart from each other.

The air bubble sensor 37 includes: the pair of piezoelectric elements 37a, 37b arranged to be spaced apart from each other; a lead wire 37c; and a substrate 37d as shown in FIGS. 18 to 24. The pair of piezoelectric elements 37a, 37b of the air bubble sensor 37 are arranged on the pump mounted part 33. Specifically, one piezoelectric element 37b is accommodated in the protruding section 34. The other piezoelectric element 37a is arranged at a position facing the protruding section 34 via the suction passage section insertion space 35, where the suction passage section 16 is inserted, therebetween.

The piezoelectric elements 37a, 37b are electrically connected to an electric circuit of the injection device main body 2 via the substrate 37d and the lead wire 37c, respectively. One of the pair of piezoelectric elements 37a, 37b functions as a transmission part for transmitting input waves including ultrasonic waves, and the other functions as a reception part for receiving the ultrasonic waves having passed through the suction passage section 16. The ultrasonic waves transmitted between the pair of piezoelectric elements 37a, 37b have an intensity and the like which varies according to the air density between the elements. Accordingly, if a gap appears between the membrane 16a and the piezoelectric elements 37a, 37b due to denting of the membrane 16a of the suction passage section 16 where no medical liquid flows, the air bubble sensor 37 including the pair of piezoelectric elements 37a, 37b can detect the absence of the medical liquid flow in the suction passage section 16 from a variation in the intensity and the like of the transmitted ultrasonic waves.

As shown in FIGS. 18 to 19, the closure sensor 38 is arranged at a position facing the protruding section 34 via the discharge passage section insertion space 36, where the discharge passage section 17 is inserted, between the closure sensor 38 and the protruding section 34. The closure sensor 38 is arranged at a position to be in contact with the membrane 17a (see FIGS. 7 and 8) which constitutes a side wall of the discharge passage section 17.

Namely, the pump mounted part 33 described above functions as "a mounted part" of the present invention for holding the air bubble sensor 37, the closure sensor 38, and the connection member 25 (a combination of the casing main body 9 and the tube connecting part 10).

In the injection device 1 configured in the manner described above, a medical liquid verification method for verifying presence of medical liquid is implemented by use of a pump casing 5 including the connection member 25 described in the present embodiment as described below.

First, as a preparation step prior to injecting medical liquid to a patient, a diaphragm pump 4 is attached to the pump attachment part 12 of the pump casing 5, and a suction tube 6 and a discharge tube 7 are attached to a suction connecting section 14 and a discharge connecting section 15 of the tube connecting part 10, respectively, thereby assembling a pump unit 3. Next, the assembled pump unit 3 is attached to the injection device main body 2, thereby arranging the pump casing 5 including the connection member 25 at a position to allow the air bubble sensor 37 for detecting presence of air to face the membrane 16a of the suction passage section 16 for preparation. Specifically, the suction passage section 16 is inserted in the suction passage section insertion space 35 of the pump mounted part 33 in such a manner that the pair of piezoelectric elements 37a, 37b of the air bubble sensor 37 and the membrane 16a face each other. Also, the discharge passage section 17 is inserted in the discharge passage section insertion space 36 of the pump mounted part 33 in such a manner that the closure sensor 38 and the membrane 17a of the discharge passage section 17 are in contact with each other.

Subsequently, a medical liquid container is connected to the suction tube 6, and a patient side tube is connected to the discharge tube 7, and thereafter, the medical liquid is injected to the patient by use of the injection device 1. At this moment, in the injection device 1 the diaphragm pump 4 pressurizes the medical liquid from the suction tube 6 to the discharge tube 7 via the connection member 25 of the pump casing 5. In that state, when the medical liquid runs out in the suction passage section 16 for a reason such as bending of the suction tube 6, air in a gap between the membrane 16a and the air bubble sensor 37 produced by denting of the membrane 16a is detected by the bubble sensor 37, thereby detecting the absence of the medical liquid. The control part (not shown) provided in the injection device main body 2 performs controls of stopping the operation of the diaphragm pump 4 and giving an alarm based on this detection signal.

Besides, when a line on the patient's side (i.e., a path on the downstream side of the discharge passage section 17) closes due to a situation where the flow of medical liquid is impeded in the patient, the membrane 17a of the discharge passage section 17 expands, and the closure sensor 38 detects a pressure rise on the membrane 17a. The control part in the injection device main body 2 performs controls of stopping the operation of the diaphragm pump 4 and giving an alarm based on this detection signal.

Feature of Present Embodiment (1)

A connection member 25 according to the present embodiment is included in a pump casing 5. The connection member 25 comprises a flow passage defining part 13 apart from a tube connecting part 10 allowing each of the suction tube 6 and the discharge tube 7 to be connected with the tube connecting part 10. The flow passage defining part 13 includes a suction passage section 16 connecting the suction port 4a of the diaphragm pump 4 and the suction connecting section 14 of the tube connecting part 10 for connection with the suction tube 6 with each other so as to flow the medical liquid between them, and a discharge passage section 17 connecting the discharge port 4b of the diaphragm pump 4 and the discharge connecting section 15 of the tube connecting part 10 for connection with the discharge tube 7 with each other so as to flow the medical liquid between them. At least a portion of each of the suction passage section 16 and the discharge passage section 17 includes membranes 16a, 17a deformable due to pressure of the medical liquid flowing in the suction passage section 16 and the discharge passage section 17. The flow passage defining part 13 has such a shape that the membranes 16a, 17a face an air bubble sensor 37 and a closure sensor 38 for detecting a flow state of the medical liquid flowing in the suction passage section 16 and the discharge passage section 17 by deformation of the membranes 16a, 17a when the flow passage defining part 13 is attached.

In the configuration described above, the suction passage section 16 and the discharge passage section 17 each allow the flow of medical liquid between either one of the suction tube 6 and the discharge tube 7 respectively connected to the suction connecting section 14 and the discharge connecting section 15 of the tube connecting part 10, and either one of the suction port 4a and the discharge port 4b of the diaphragm pump 4 both attached to the pump attachment part 12. When the membranes 16a, 17a, which each constitute at least a portion of each of the suction passage section 16 and the discharge passage section 17, deform due to pressure of the medical liquid flowing in the suction passage section 16 and the discharge passage section 17, the air bubble sensor 37 and the closure sensor 38, which face the membranes 16a, 17a, can detect a flow state of the medical liquid flowing in the suction passage section 16 and the discharge passage section 17 by deformation of the membranes 16a, 17a. The flow state of the medical liquid can be thus detected by use of the air bubble sensor 37 and the closure sensor 38 without involving limitations on the material, the tube thickness, the tube diameter or the like of the suction tube 6 and the discharge tube 7. This enables various kinds of tubes to be used, and thus enables a tube having a material or a thickness hardly deformable to be used as the suction tube 6 and the discharge tube 7, thereby suppressing the tubes from bending.

Further, in the present configuration, the flow state of the medical liquid can be detected by the air bubble sensor 37 and the closure sensor 38 as long as the membranes 16a, 17a of the suction passage section 16 and the discharge passage section 17 are at the corresponding positions to the air bubble sensor 37 and the closure sensor 38. This configuration enables the suction tube 6 and the discharge tube 7 to be connected to the tube connecting part 10 without consideration of the positional relationship to the air bubble sensor 37 and the closure sensor 38. The trouble in the tube attachment is thus eliminated.

(2)

Besides, in the connection member 25 according to the present embodiment, the flow passage defining part 13 includes: a suction sealing portion 22 formed integrally with the suction passage section 16 for ensuring liquid-tight sealing between the suction port 4a of the diaphragm pump 4 and the suction opening 12b of the pump attachment part 12; and a discharge sealing portion 23 formed integrally with the discharge passage section 17 for ensuring liquid-tight sealing between the discharge port 4b of the diaphragm pump 4 and the discharge opening 12c of the pump attachment part 12.

Owing to this configuration, the flow passage defining part 13 includes a sealing portion 22, 23 on each of the suction side and the discharge side. The leak of the medical liquid at the suction port 4a and the discharge port 4b of the diaphragm pump 4 can be thus prevented.

Additionally, the membranes 16a, 17a and the sealing portions 22, 23 at each of the suction side and the discharge side are integrally formed by an elastic material (for example, a silicone rubber and the like). The number of parts can be thus prevented from increasing.

(3)

Further, in the connection member 25 according to the present embodiment, a combination of the membrane 16a of the suction passage section 16 and the suction sealing portion 22 and a combination of the membrane 17a of the discharge passage section 17 and the discharge sealing portion 23 each form a cylindrical member. The suction passage section 16 and the discharge passage section 17 can be thus formed in a cylindrical shape. This simplifies the structure of the suction passage section 16 and the discharge passage section 17, and can further realize a smooth flow of medical liquid in the suction passage section 16 and the discharge passage section 17.

(4)

Additionally, in the connection member 25 according to the present embodiment, the tube connecting part 10 includes a cylindrical suction connecting section 14 to be connected to the suction tube 6 and a cylindrical discharge connecting section 15 to be connected to the discharge tube 7. A suction flow passage 18 is defined between the suction connecting section 14 and the membrane 16a of the suction passage section 16 which covers the suction connecting section 14. A discharge flow passage 19 is defined between the discharge connecting section 15 and the membrane 17a of the discharge passage section 17 which covers the discharge connecting section 15. This configuration can prevent air bubble from staying near the membranes 16a, 17a on both the suction side and the discharge side.

(5)

The connection member 25 according to the embodiment described above comprises a gap 13a (fitting section) operable to fit to a protruding section 34 (fitted section) of an injection device main body 2 holding the air bubble sensor 37 and the closure sensor 38 in a state where the membranes 16a, 17a face the sensors.

This configuration enables easy setting of the membranes 16a, 17a at positions facing the sensor 37, 38 described above by merely fitting the gap 13a (fitting section) of the connection member 25 to the protruding section 34 (fitted section) of the injection device main body 2.

(6)

Further, the connection member 25 according to the present embodiment comprises a restricting section 12d for keeping the gap 13a (fitting section) from fitting to the protruding section 34 (fitted section) in a state where the membranes 16a, 17a do not face the air bubble sensor 37 and the closure sensor 38. This configuration can prevent the pump casing 5 (particularly, the connection member 25 included in the pump casing 5) from being mounted in an incorrect direction when being mounted in the injection device main body 2. Specifically, even in an attempt to mount the pump casing 5 in the pump mounted part 33 (see FIGS. 18 to 19) in a posture of upside down, the protruding section 34 interferes with the restricting section 12d (see FIGS. 3 and 8) provided on a rear side portion of the pump attachment part 12 of the casing main body 9, thereby securely preventing an incorrect mounting of the casing 5.

(7)

The pump casing 5 according to the present embodiment comprises the connection member 25 described above and a lid member 11 for closing a rectangular-shaped recess section 12a in the pump attachment part 12 in which the diaphragm pump 4 is inserted as shown in FIGS. 2 to 3, 9, and 15 to 17. The recess section 12a in the present invention is not limited to a rectangular shape, and may have other shape than the rectangular shape.

The suction sealing portion 22 and the discharge sealing portion 23 have the same height, and are arranged on one diagonal of the recess section 12a. According to the present invention, the suction sealing portion 22 and the discharge sealing portion 23 are not limited to be arranged on the one diagonal of the recess section 12a, and may be placed in other arrangement.

A pair of pump fixing portions 26, 27 having the same height as the suction sealing portion 22 and the discharge sealing portion 23 are provided on the other diagonal of the recess section 12a. According to the present invention, it may be sufficient to provide at least one pump fixing portion, but the present invention is not limited to the arrangement that the pair are on the other diagonal of the recess section 12a.

Figure 9:
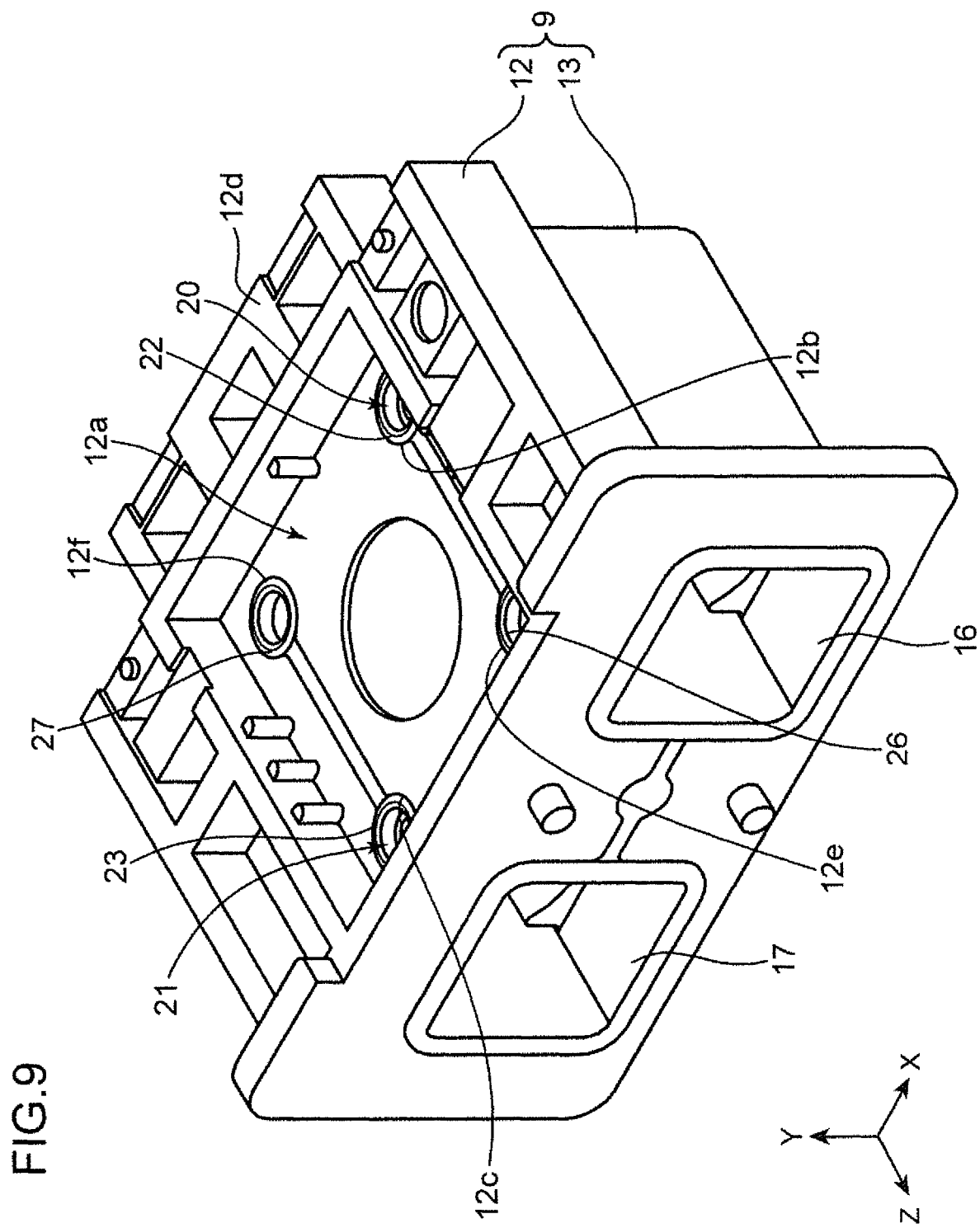
FIG. 9 is a perspective view of a casing main body shown in FIG. 3.
Figure 15:
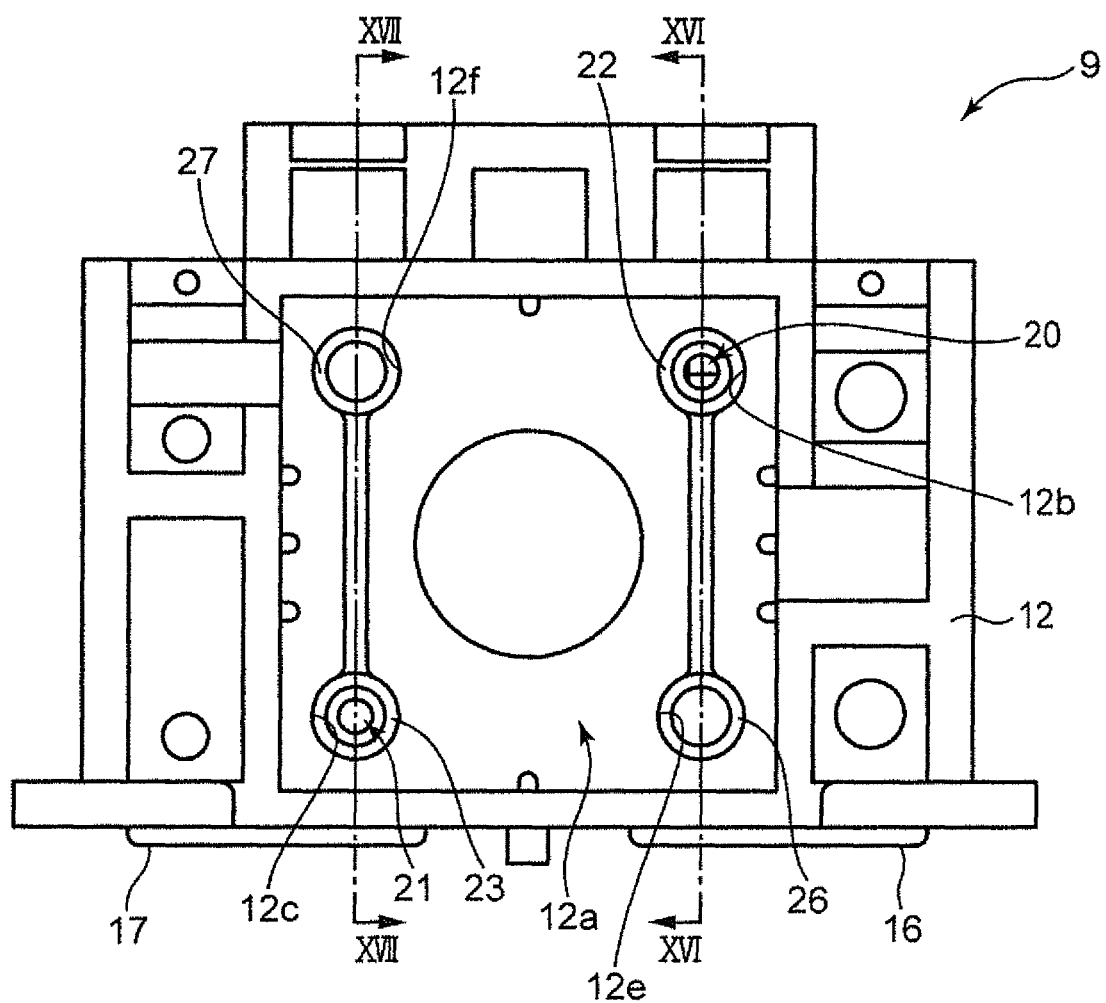
FIG. 15 is a plan view of the casing main body shown in FIG. 9.
Figure 16:
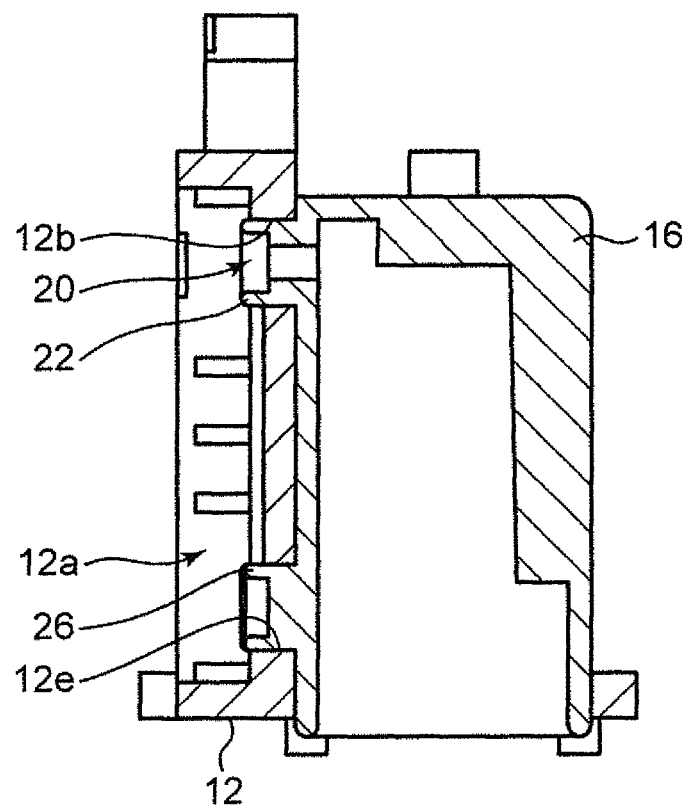
FIG. 16 is a cross sectional view taken along the line XVI-XVI in FIG. 15.
Figure 17:
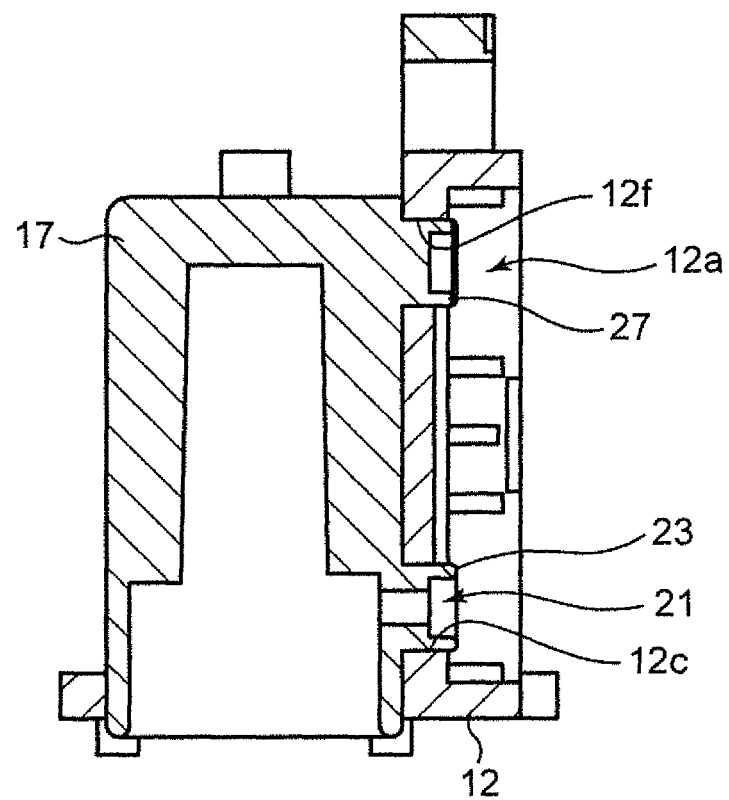
FIG. 17 is a cross sectional view taken along the line XVII-XVII in FIG. 15.

The suction sealing portion 22, the discharge sealing portion 23, and the pair of pump fixing portions 26, 27 are arranged in the square form as shown in FIGS. 9 and 15.

Figure 3:
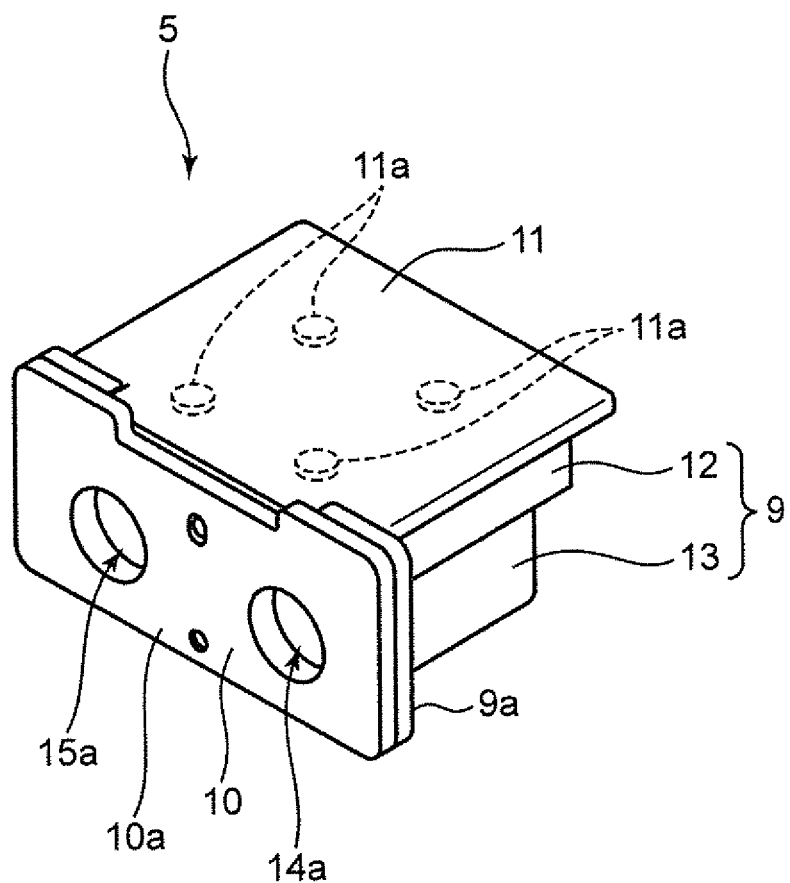
FIG. 3 is a perspective view of a pump casing shown in FIG. 2.
Figure 4:
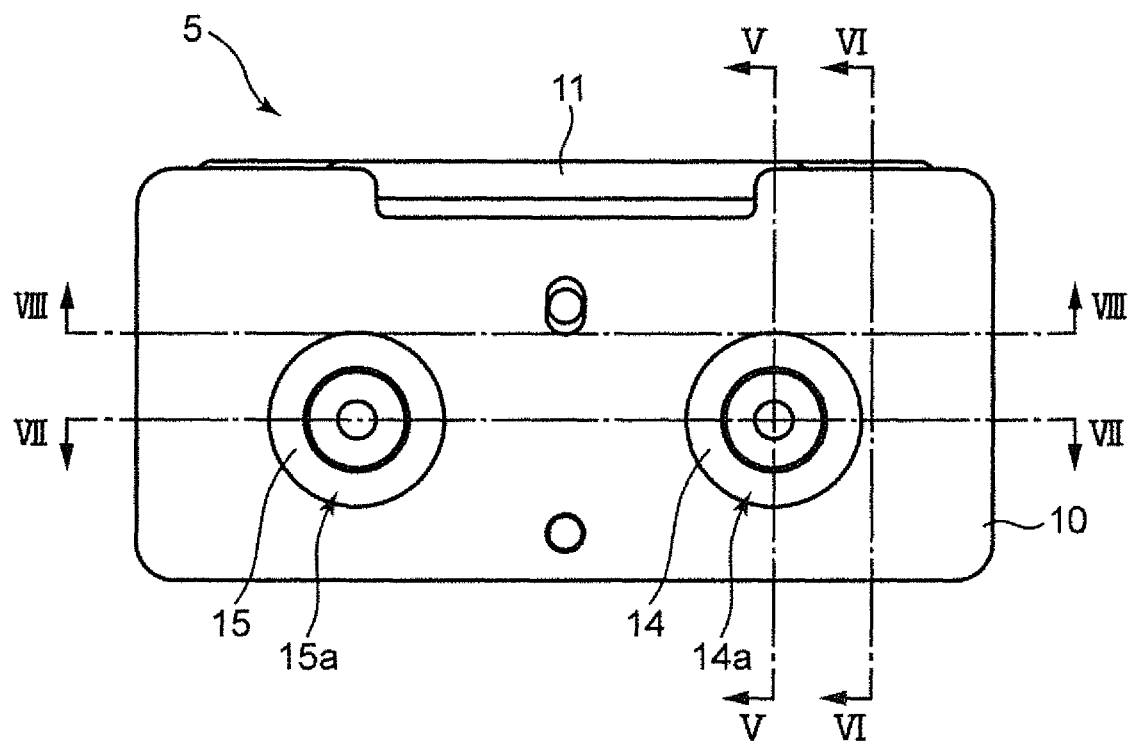
FIG. 4 is a front view of the pump casing shown in FIG. 3.
Figure 5:
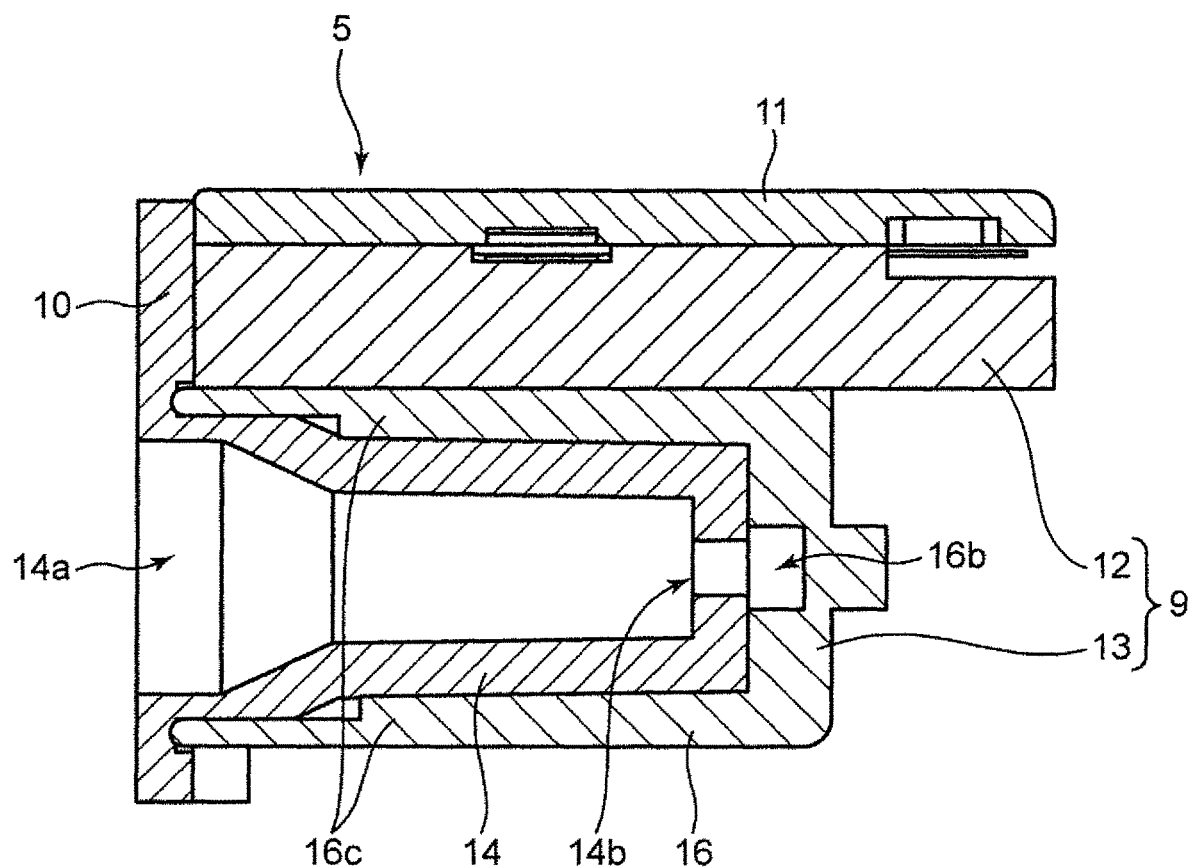
FIG. 5 is a cross sectional view taken along the line V-V in FIG. 4.
Figure 6:
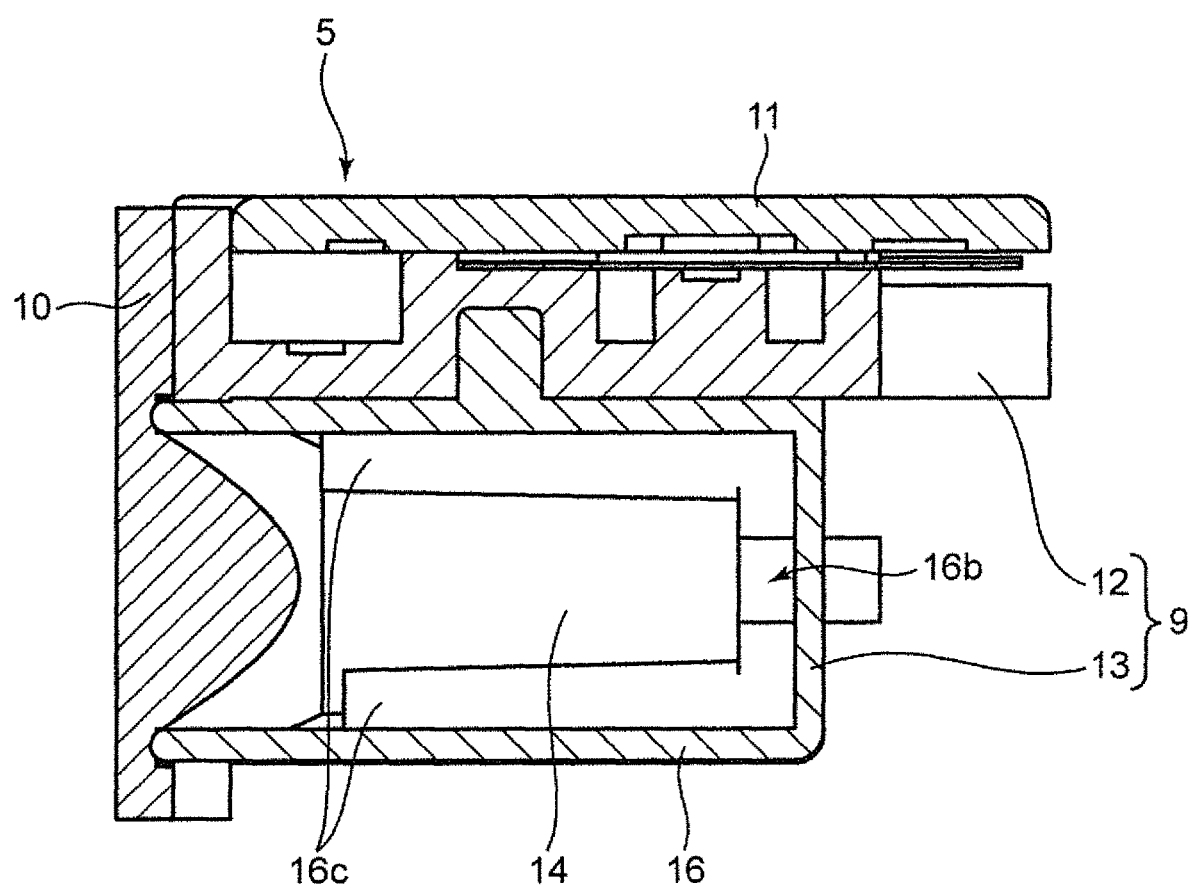
FIG. 6 is a cross sectional view taken along the line VI-VI in FIG. 4.

The lid member 11 is provided with protrusions 11a respectively protruding toward the suction sealing portion 22, the discharge sealing portion 23, and the pair of pump fixing portions 26, 27 as shown in FIG. 3. Namely, the protrusions 11a protrude downward from a lower surface of the lid member 11 at positions corresponding to the sealing portions 22, 23, and the pair of pump fixing portions 26, 27.

Owing to the configuration described above, the pump casing 5 can support the diaphragm pump 4 to be inserted in the recess section 12a of the pump attachment part 12 at at least three positions in a state where the diaphragm pump 4 is sandwiched between either one of the suction sealing portion 22, the discharge sealing portion 23, and at least one (a pair of in the present embodiment) pump fixing portion 26, 27 and the protrusions 11a of the lid member 11 respectively facing them (in the present embodiment, the diaphragm pump 4 can be vertically supported at four points). As a result, the diaphragm pump 4 can be prevented from deforming.

(8)

In the pump casing 5 according to the present embodiment, the pump fixing portions 26, 27 protrude in the recess section 12a through the openings 12e, 12f formed in the pump attachment part 12 as shown in FIGS. 9, and 15 to 17. The pump fixing portions 26, 27 are formed (of a silicone rubber and the like) integrally with the suction passage section 16 and the discharge passage section 17 together with the suction sealing portion 22 and the discharge sealing portion 23. This configuration can prevent the number of parts from increasing.

(9)

In the present embodiment, the diaphragm pump 4 includes a stationary section 4c (specifically, a flame section) which is immovable when the liquid is pressurized and fed, and a movable section 4d (specifically, a diaphragm which expands and contracts up and down) as shown in FIG. 2. The suction port 4a and a discharge port 4b of the diaphragm pump 4 are arranged in the stationary section 4c. On the other hand, in the pump casing 5, the suction sealing portion 22, the discharge sealing portion 23, and the pump fixing portions 26, 27 are at positions where they come into contact with one surface (lower surface in the present embodiment) of the stationary section 4c in a state where the diaphragm pump 4 is in the recess section 12a of the pump attachment part 12 as shown in FIGS. 9, and 15. Further, the protrusions 11a of the lid member 11 are at a position where it comes into contact with the other surface (upper surface in the present embodiment) of the stationary section 4c in the state where the diaphragm pump 4 is inserted in the recess section 12a as shown in FIG. 3.

This configuration enables the suction sealing portion 22, the discharge sealing portion 23, and the pair of pump fixing portions 26, 27 to come into contact with one surface (lower surface) of the stationary section 4c of the diaphragm pump 4, and the protrusions 11a of the lid member 11 to come into contact with the other surface (upper surface) in the state where the diaphragm pump 4 is inserted in the recess section 12a. Owing to this configuration, the stationary section 4c of the diaphragm pump 4 can be supported at at least three positions (at four positions in the present embodiment) in a state where the stationary section 4c of the diaphragm pump 4 is sandwiched between either one of the suction sealing portion 22, the discharge sealing portion 23, and the pair of pump fixing portions 26, 27 and the protrusions of the lid member respectively facing them. As a result, the diaphragm pump 4 can be further securely prevented from deforming.

In particular, in the present embodiment, the suction sealing portion 22, the discharge sealing portion 23, and the pair of pump fixing portions 26, 27 are arranged on two diagonals in the square form. Thus, the four corners of the stationary section 4c of the diaphragm pump 4 having the shape of a square can be stably supported.

(10)

The injection device 1 according to the present embodiment comprises: a diaphragm pump 4 for pressurizing and feeding the medical liquid; a suction tube 6; a discharge tube 7; a pump casing 5 including the connection member 25 according to the embodiment described above; and an injection device main body 2 including a pump mounted part 33 (mounted part) for holding the pump casing 5. The connection member 25 includes a gap 13a (fitting section) operable to fit to a protruding section 34 (fitted section) of the injection device main body 2 for holding the air bubble sensor 37 and the closure sensor 38 in a state where the membranes 16a, 17a face the sensors.

In this configuration of the injection device 1, the air bubble sensor 37 and the closure sensor 38 are concentratedly arranged in the pump mounted part 33 (mounted part) of the injection device main body 2. Thus, the air bubble sensor 37 and the closure sensor 38 can be mounted on the connection member 25, in other words, each of the air bubble sensor 37 and the closure sensor 38 can be accurately arranged at a predetermined position of the connection member 25 by merely placing the pump casing 5 including the connection member 25 for connecting the suction tube 6 and the discharge tube 7 to the diaphragm pump 4 in the pump mounted part 33.

In the embodiment described above, the air bubble sensor 37 and the closure sensor 38 are described as an example of a sensor for detecting the flow state of the medical liquid (liquid) flowing in the suction passage section 16 and the discharge passage section 17 by deformation of the membranes 16a, 17a. However, the present invention is not limited to these. In the present invention, other kinds of sensor can be used as long as it is a sensor for detecting the flow state of liquid by deformation of the membranes 16a, 17a of the suction passage section 16 and the discharge passage section 17.

(11)

In a method for verifying medical liquid by use of a pump casing 5 including a connection member 25 according to the present embodiment comprises two steps (a) and (b), namely:

(a) a preparation step of disposing the pump casing 5 including the connection member 25 in a position to allow the membranes 16*a* of the suction passage section 16 to face the air bubble sensor 37 for detecting presence of air in a state where the diaphragm pump 4 is attached to the pump attachment part 12 and the suction tube 6 and the discharge tube 7 are respectively attached to the suction connecting section 14 and the discharge connecting section 15 of the tube connecting part 10; and (b) a detection step of detecting an absence of the medical liquid by detecting, with the sensor, air in a gap produced between the membrane 16*a* and the air bubble sensor 37 by denting of the membrane 16*a* due to run-out of the medical liquid in the suction passage section 16 during a time when the diaphragm pump 4 pressurizes and feeds the medical liquid from the suction tube 6 to the discharge tube 7 through the pump casing 5 including the connection member 25.

This method for verifying medical liquid makes it possible to easily and accurately detect based on the detection of air in a gap between the membrane 16*a* and the air bubble sensor 37 by a sensor such as the air bubble sensor 37 for detecting presence of air that no medical liquid flows in the suction passage section 16. This configuration eliminates the use of an expensive sensor such as a pressure sensor and a flow rate sensor.

Summary of Embodiment

The embodiment described above will be summarized hereinafter.

A connection member according to the embodiment described above is to be provided between a pump for pressurizing and feeding liquid and a suction tube for connecting a suction port of the pump with the suction tube, and between the pump and a discharge tube for connecting a discharge port of the pump with the discharge tube, comprising: a pump attachment part which includes a suction opening for connection with the suction port and a discharge opening for connection with the discharge port, and which is attached with the pump in a state where the suction port is connected to the suction opening and the discharge port is connected to the discharge opening; a tube connecting part including a suction connecting section for connecting the suction tube and a discharge connecting section for connecting the discharge tube; and a flow passage defining part including a suction passage section and a discharge passage section, the suction passage section connecting the suction opening of the pump attachment part and the suction connecting section of the tube connecting part with each other so as to flow the liquid between the suction opening and the suction connecting section, and the discharge passage section connecting the discharge opening of the pump attachment part and the discharge connecting section of the tube connecting part with each other so as to flow the liquid between the discharge opening and the discharge connecting section, wherein at least a portion of each of the suction passage section and the discharge passage section includes a membrane deformable due to pressure of the liquid flowing in the suction passage section and the discharge passage section, and the flow passage defining part has a shape allowing the flow passage defining part to be attached to a sensor for detecting a flow state of the liquid flowing in the suction passage section and the discharge passage section by deformation of the membranes in an arrangement that the membranes face the sensor.

Owing to this configuration, the suction passage section and the discharge passage section each allow the flow of liquid between either one of the suction tube and the discharge tube respectively connected to the suction connecting section and the discharge connecting section of the tube connecting part, and either one of the suction port and the discharge port of the pump both attached to the pump attachment part. When the membrane, which constitutes at least a portion of each of the suction passage section and the discharge passage section, deforms due to pressure of the liquid flowing in the suction passage section and the discharge passage section, the sensor, which faces the membranes, can detect a flow state of the liquid flowing in the suction passage section and the discharge passage section by deformation of the membranes. The flow state of the liquid can be thus detected by use of the sensor without involving limitations on material, thickness, and diameter of the suction tube and the discharge tube. This enables various kinds of tubes to be used.

Further, in the present configuration, the flow of the liquid can be detected by the sensor as long as the membranes of the suction passage section and the discharge passage section are at the corresponding positions to the sensor. This configuration enables the suction tube and the discharge tube to be connected to the tube connecting part without consideration of the positional relationship to the sensor. The trouble in the tube attachment is thus eliminated.

Preferably, the flow passage defining part includes: a suction sealing portion formed integrally with the suction passage section for ensuring liquid-tight sealing between the suction port of the pump and the suction opening of the pump attachment part; and a discharge sealing portion formed integrally with the discharge passage section for ensuring liquid-tight sealing between the discharge port of the pump and the discharge opening of the pump attachment part.

Owing to this configuration, the flow passage defining part includes a sealing portion on each of the suction side and the discharge side. The leak of the liquid at the suction port and the discharge port of the pump can be thus prevented.

Additionally, the membranes and the sealing portions at each of the suction side and the discharge side are integrally formed. The number of parts can be thus prevented from increasing.

Preferably, a combination of the membrane of the suction passage section and the suction sealing portion and a combination of the membrane of the discharge passage section and the discharge sealing portion each form a cylindrical member.

Owing to this configuration, the membrane and the sealing portion form a cylindrical member on the suction side and the discharge side of the flow passage defining part. The suction passage section and the discharge passage section can be thus formed in a cylindrical shape. This simplifies the structure of the suction passage section and the discharge passage section, and can further realize a smooth flow of liquid in the suction passage section and the discharge passage section.

Preferably, the suction connecting section and the discharge connecting section each have the shape of a cylinder, the membrane of the suction passage section covers a periphery of the suction connecting section with a gap to define a suction flow passage between the suction connecting section and the membrane of the suction passage section, and the membrane of the discharge passage section covers a periphery of the discharge connecting section with a gap to define a discharge flow passage between the discharge connecting section and the membrane of the discharge passage section.

Owing to this configuration, a suction flow passage is defined between a cylindrical suction connecting section to be connected to the suction tube and the membrane of the suction passage section which covers the suction connecting section, and a discharge flow passage is defined between a cylindrical discharge connecting section to be connected to the discharge tube and the membrane of the discharge passage section which covers the discharge connecting section. This configuration can prevent air bubble from staying near the membranes on both the suction side and the discharge side.

Preferably, the connection member further comprises: a fitting section for fitting to a fitted section of an injection device main body which holds the sensor in a state where the membranes face the sensor.

This configuration enables easy setting of the membranes at positions facing the sensor by merely fitting the fitting section of the connection member to the fitted section of the injection device main body.

Preferably, the connection member further comprises: a restricting section for keeping the fitting section from fitting to the fitted section in a state where the membranes do not face the sensor.

This configuration can prevent the connection member from being mounted in an incorrect direction when being mounted in the injection device main body.

The pump casing according to the present embodiment comprises the connection member including the flow passage defining part having: a suction sealing portion formed integrally with the suction passage section for ensuring liquid-tight sealing between the suction port of the pump and the suction opening of the pump attachment part; and a discharge sealing portion formed integrally with the discharge passage section for ensuring liquid-tight sealing between the discharge port of the pump and the discharge opening of the pump attachment part; and a lid member for closing a recess section of the pump attachment par, the recces section being for that the pump is inserted, wherein the suction sealing portion and the discharge sealing portion have the same height, the recess section is provided with at least one pump fixing portion having the same height as each height of the suction sealing portion and the discharge sealing portion, and the lid member has protrusions respectively protruding toward the suction sealing portion, the discharge sealing portion, and the pump fixing portion.

This configuration enables to support the pump to be inserted in the recess section of the pump attachment part at least three positions in a state where the pump is sandwiched between either one of the suction sealing portion, the discharge sealing portion, and at least one pump fixing portion and the protrusions of the lid member respectively facing them. As a result, the pump can be prevented from deforming.

Preferably, the pump fixing portion protrudes in the recess section through an opening formed in the pump attachment part, and the pump fixing portion is formed integrally with the suction passage section and the discharge passage section together with the suction sealing portion and the discharge sealing portion.

This configuration can prevent the number of parts from increasing.

Preferably, the pump includes a stationary section which is immovable when the liquid is pressurized and fed, the suction port and the discharge port are located on the stationary section, the suction sealing portion, the discharge sealing portion, and the pump fixing portion are positioned at a position to be in contact with one surface of the stationary section in a state where the pump is inserted in the recess section, and the protrusions of the lid member are at a position to be in contact with the other surface of the stationary section in the state where the pump is inserted in the recess section.

This configuration enables the suction sealing portion, the discharge sealing portion, and the pump fixing portion to come into contact with one surface of the stationary section of the pump, and the protrusions of the lid member to come into contact with the other surface in the state where the pump is inserted in the recess section. Owing to this configuration, the stationary section of the pump can be supported at least three positions in a state where the stationary section of the pump is sandwiched between either one of the suction sealing portion, the discharge sealing portion, and the pump fixing portion and the protrusions of the lid member respectively facing them. As a result, the pump can be further securely prevented from deforming.

An injection device according to the present embodiment comprises: a pump for pressurizing and feeding the liquid; a suction tube; a discharge tube; the connection member; and an injection device main body which holds the sensor and includes a mounted part on which the connection member is mounted, wherein the connection member includes a fitting section for fitting to a fitted section provided in the mounted part in a state where the membranes face the sensor.

Owing to this configuration, the sensors are concentratedly arranged in the mounted part of the injection device main body. Thus, the sensors can be mounted on the connection member, in other words, each of the sensors can be accurately arranged at a predetermined position of the connection member by merely placing the connection member for connecting the suction tube and the discharge tube to the pump in the mounted part.

A method for verifying liquid according to the present embodiment is for verifying presence of liquid by use of the connection member, and comprises: a preparation step of disposing the connection member in a position to allow the sensor for detecting presence of air to face the membrane of the suction passage section in a state where the pump is attached to the pump attachment part and further the suction tube and the discharge tube are respectively attached to the suction connecting section and the discharge connecting section of the tube connecting part; and a detection step of detecting an absence of the liquid by detecting air in a gap produced between the membranes and the sensor by denting of the membranes due to run-out of the liquid in the suction passage section during a time when the pump pressurizes and feeds the liquid from the suction tube to the discharge tube through the connection member.

This configuration makes it possible to easily and accurately detect based on the detection of air in a gap between the membranes and the sensor by a sensor such as the air bubble sensor for detecting presence of air that no liquid flows in the suction passage section. This configuration eliminates the use of an expensive sensor such as a pressure sensor and a flow rate sensor.

As described above, a connection member according to the present embodiment will is not limited by the material, the tube thickness, the tube diameter or the like of a suction tube and a discharge tube to be connected to a pump, and can eliminate the troubles in the tube attachment.

The invention claimed is:

1. A connection member to be provided between a pump for pressurizing and feeding liquid and a suction tube for connecting a suction port of the pump with the suction tube, and between the pump and a discharge tube for connecting a discharge port of the pump with the discharge tube, comprising:
a casing main body; and
a tube connecting part, wherein
the casing main body includes a pump attachment part and a flow passage defining part,
the pump attachment part includes an upper surface provided with a suction opening for connection with the suction port which opens in a bottom wall of the pump and a discharge opening for connection with the discharge port which opens in the bottom wall of the pump, the pump attachment part being configured to be attached with the pump on the upper surface of the pump attachment part in a state in which the suction port is connected to the suction opening and the discharge port is connected to the discharge opening,
the tube connecting part is attached to the casing main body in front of a front surface of the casing main body,
the tube connecting part includes a suction connecting section for connecting to the suction tube and a discharge connecting section for connecting to the discharge tube,
the suction connecting section and the discharge connecting section have respective tube connecting ports where the suction tube and the discharge tube are to be respectively inserted and then fixed in a front of the tube connecting part,
the flow passage defining part includes a suction passage section and a discharge passage section, the suction passage section connecting the suction opening of the pump attachment part and the suction connecting section of the tube connecting part with each other so as to flow the liquid between the suction opening and the suction connecting section, and the discharge passage section connecting the discharge opening of the pump attachment part and the discharge connecting section of the tube connecting part with each other so as to flow the liquid between the discharge opening and the discharge connecting section,
at least a portion of the suction passage section includes a first membrane, at least a portion of the discharge passage section includes a second membrane, the first and second membranes being deformable due to pressure of the liquid flowing in the suction passage section and the discharge passage section, respectively, and
the flow passage defining part has a shape which allows the flow passage defining part to be attached to a sensor for detecting a flow state of the liquid flowing in the suction passage section and the discharge passage section by deformation of at least one of the first and second membranes in an arrangement in which the first and second membranes face the sensor.

2. The connection member according to claim 1, wherein the flow passage defining part includes:
a suction sealing portion formed integrally with the suction passage section for ensuring liquid-tight sealing between the suction port of the pump and the suction opening of the pump attachment part; and
a discharge sealing portion formed integrally with the discharge passage section for ensuring liquid-tight sealing between the discharge port of the pump and the discharge opening of the pump attachment part.

3. The connection member according to claim 2, wherein a combination of the first membrane of the suction passage section and the suction sealing portion, and a combination of the second membrane of the discharge passage section and the discharge sealing portion, each form a cylindrical member.

4. The connection member according to claim 1, wherein the suction connecting section and the discharge connecting section each have the shape of a cylinder,
the first membrane of the suction passage section covers a periphery of the suction connecting section with a gap therebetween to define a suction flow passage between the suction connecting section and the first membrane of the suction passage section, and
the second membrane of the discharge passage section covers a periphery of the discharge connecting section with a gap therebetween to define a discharge flow passage between the discharge connecting section and the second membrane of the discharge passage section.

5. The connection member according to claim 1, further comprising:
a fitting section configured to be fitted to a fitted section of an injection device main body which holds the sensor in a state in which the first and second membranes face the sensor.

6. The connection member according to claim 5, further comprising:
a restricting section configured to prevent the fitting section from being fitted to the fitted section in a state in which the first and second membranes do not face the sensor.

7. The connection member according to claim 5, wherein the fitting section is formed as a gap between the suction passage section and the discharge passage section in the flow passage defining part.

8. A pump casing, comprising:
the connection member according to claim 2; and
a lid member for closing a recess section of the pump attachment part, the recess section being configured to accommodate the pump therein, wherein
the suction sealing portion and the discharge sealing portion each have a same height,
the recess section is provided with at least one pump fixing portion having a height which is the same as each height of the suction sealing portion and the discharge sealing portion, and
the lid member has protrusions respectively protruding toward the suction sealing portion, the discharge sealing portion, and the at least one pump fixing portion.

9. The pump casing according to claim 8, wherein the at least one pump fixing portion protrudes in the recess section through an opening formed in the pump attachment part, and
the at least one pump fixing portion is formed integrally with the suction passage section and the discharge passage section together with the suction sealing portion and the discharge sealing portion.

10. The pump casing according to claim 8, wherein the pump includes a stationary section which is immovable when the liquid is pressurized and fed,
the suction port and the discharge port are located on the stationary section,
the suction sealing portion, the discharge sealing portion, and the at least one pump fixing portion are positioned so as to be in contact with a first surface of the stationary section in a state in which the pump is inserted in the recess section, and the protrusions of the lid member are positioned so as to be in contact with a second surface of the stationary section in the state in which the pump is inserted in the recess section, the first and second surfaces being opposite surfaces of the stationary section.

11. An injection device for injecting liquid into an injection target, comprising:
- a pump for pressurizing and feeding the liquid;
- a suction tube;
- a discharge tube;
- the connection member according to claim 1; and
- an injection device main body which holds the sensor and includes a mounted part on which the connection member is mounted, wherein
- the connection member includes a fitting section fitted to a fitted section provided in the mounted part, in a state in which the first and second membrane face the sensor.

12. A method for verifying presence of liquid by use of the connection member according to claim 1, comprising:
- disposing the connection member in a position to allow the sensor to face the membrane of the suction passage section in a state in which the pump is attached to the pump attachment part and in which the suction tube and the discharge tube are respectively attached to the suction connecting section and the discharge connecting section of the tube connecting part, wherein the sensor is configured to detect presence of air; and
- detecting an absence of the liquid by detecting, with the sensor, air in a gap produced between the first membrane and the sensor by denting of the first membrane due to run-out of the liquid in the suction passage section during a time when the pump pressurizes and feeds the liquid from the suction tube to the discharge tube through the connection member.

* * * * *